United States Patent
Croxton et al.

(10) Patent No.: US 7,682,398 B2
(45) Date of Patent: Mar. 23, 2010

(54) VARIABLE GEOMETRY RIM SURFACE ACETABULAR SHELL LINER

(75) Inventors: Michael A. Croxton, Germantown, TN (US); Brian W. McKinnon, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 100 days.

(21) Appl. No.: 11/605,921

(22) Filed: Nov. 28, 2006

(65) Prior Publication Data

US 2007/0106389 A1    May 10, 2007

Related U.S. Application Data

(63) Continuation-in-part of application No. 11/456,475, filed on Jul. 10, 2006, now abandoned, which is a continuation of application No. 09/808,228, filed on Mar. 14, 2001, now Pat. No. 7,074,241.

(60) Provisional application No. 60/189,182, filed on Mar. 14, 2000.

(51) Int. Cl.
*A61F 2/32* (2006.01)
(52) U.S. Cl. ............................... 623/22.24; 623/22.21
(58) Field of Classification Search ... 623/22.15–22.19, 623/22.21, 22.39, 23.43
See application file for complete search history.

(56) References Cited

U.S. PATENT DOCUMENTS

| | | | | |
|---|---|---|---|---|
| 4,437,193 A | | 3/1984 | Oh | |
| 4,642,123 A | * | 2/1987 | Noiles | 623/22.2 |
| 4,795,469 A | | 1/1989 | Oh | |
| 5,226,917 A | | 7/1993 | Schryver | |
| 5,263,988 A | * | 11/1993 | Huebner | 623/22.29 |
| 5,310,408 A | | 5/1994 | Schryver et al. | |
| 5,314,487 A | | 5/1994 | Schryver et al. | |
| 5,443,519 A | | 8/1995 | Averill et al. | |
| 5,507,824 A | | 4/1996 | Lennos | |
| 5,702,477 A | | 12/1997 | Capello et al. | |
| 5,782,928 A | | 7/1998 | Ries et al. | |

(Continued)

FOREIGN PATENT DOCUMENTS

DE    44 28 407 A1    2/1996

(Continued)

OTHER PUBLICATIONS

T. Cobb, et al., The Elevated-Rim Acetabular Liner in Total Hip Arthroplasty: Relationship to Postoperative Dislocation, *Journal of Bone and Joint Surgery*, vol. 78-A, No. 1, Jan. 1996, pp. 80-86.

(Continued)

*Primary Examiner*—Corrine M McDermott
*Assistant Examiner*—Megan Wolf
(74) *Attorney, Agent, or Firm*—Kilpatrick Stockton LLP

(57) ABSTRACT

There is provided an acetabular shell liner, and particularly a constrained liner, having a variable rim surface geometry to improve the range of motion of a femoral component within the liner and decrease the incidence of dislocation and subluxation. There are also provided methods of making and using the acetabular shell liner. Prosthetic devices, and particularly hip joint prostheses, containing the acetabular shell liner having a variable rim surface geometry are also provided.

26 Claims, 20 Drawing Sheets

U.S. PATENT DOCUMENTS

| | | | |
|---|---|---|---|
| 5,800,555 A | 9/1998 | Gray, III | |
| 5,879,399 A * | 3/1999 | Church | 623/22.25 |
| 5,879,404 A | 3/1999 | Bateman et al. | |
| 5,904,720 A | 5/1999 | Farrar et al. | |
| 5,972,032 A | 10/1999 | Lopez et al. | |
| 7,074,241 B2 | 7/2006 | McKinnon | |
| 2002/0068980 A1 | 6/2002 | Serbousek et al. | |
| 2005/0261777 A1 | 11/2005 | Jones et al. | |
| 2008/0255672 A1 | 10/2008 | Gil | |

FOREIGN PATENT DOCUMENTS

| | | |
|---|---|---|
| EP | 0 901 777 A2 | 3/1999 |
| WO | WO 96/04866 | 2/1996 |
| WO | WO 01/67999 | 9/2001 |

OTHER PUBLICATIONS

B. McGrory, et al., Correlation of Measured Range of Hip Motion Following Total Hip Arthroplasty and Responses to a Questionnaire, *Journal of Arthroplasty*, vol. II, No. 5, 1996.

Thornberry, et al., The Effects of Neck Geometry and Acetabular Design on the Motion to Impingement in Total Hip Replacement, A Scientific Exhibit at the 1998 AAOS Meeting, New Orleans, Louisiana, 1998.

Brochure entitled 'Reflection Lateralized Liners . . . Reflection Acetabular System,' Smith & Nephew (May 1977).

Brochure entitled 'Reflection Interfit . . . Porous-Coated Acetabular Component,' Smith & Nephew Surgical Technique, pp. 1-20 (Jan. 1999).

James W. Harkess, et al., Variations in Design of Anteverted Acetabular Liners in THR, A Scientific Exhibit at the 2000 AAOS Meeting, Orange County, California, Mar. 15-19, 2000, publication made available at least as early as Feb. 17, 2000.

* cited by examiner

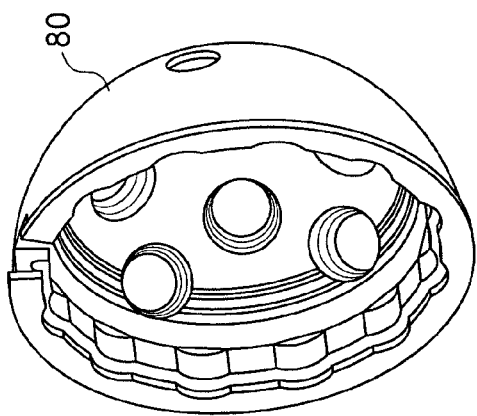
FIG. 10
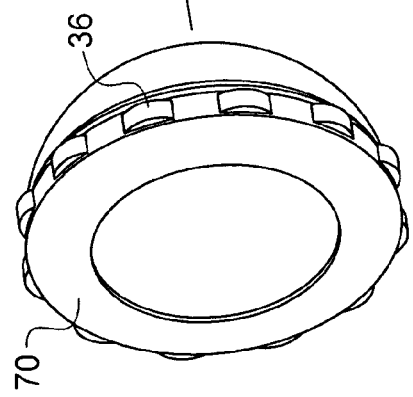
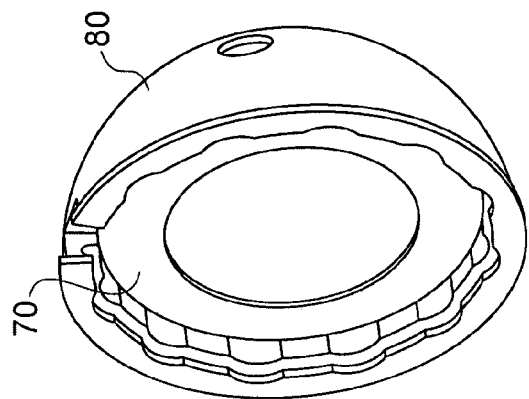
FIG. 11

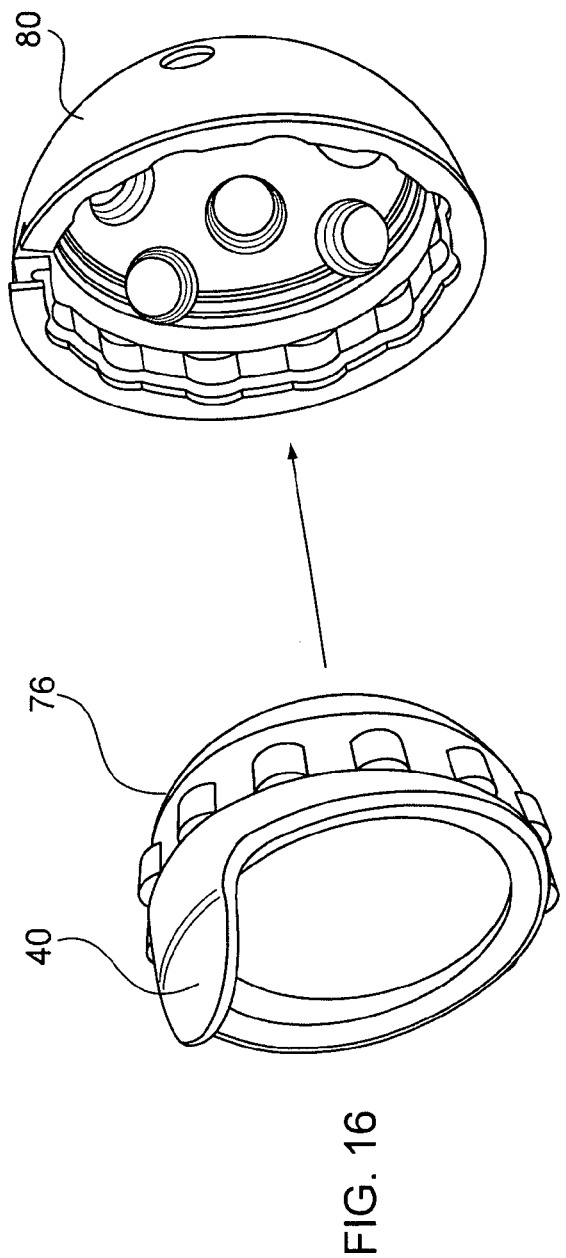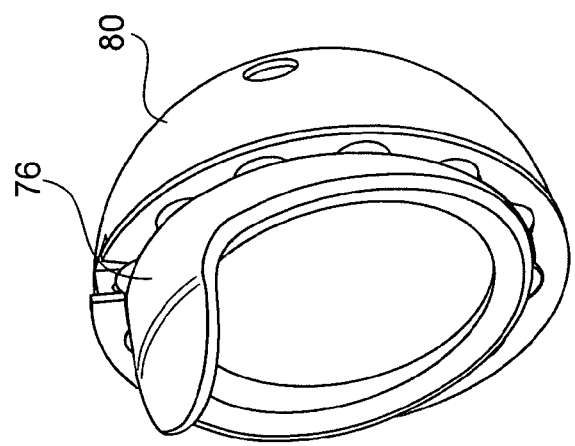

VARIABLE GEOMETRY RIM SURFACE ACETABULAR SHELL LINER

This application is a continuation-in-part and claims the benefit of U.S. non-provisional application Ser. No. 11/456,475, filed Jul 10, 2006, titled "Variable Geometry Rim Surface Acetabular Shell Liner," now abandoned, which is a continuation application that claims the benefit of U.S. non-provisional application Ser. No. 09/808,228, filed Mar. 14, 2001 titled "Variable Geometry Rim Surface Acetabular Shell Liner," now U.S. Pat. No. 7,074,241, which claims the benefit of U.S. Provisional Application Ser. No. 60/189,182, filed on Mar. 14, 2000, the entire contents of each of which are hereby incorporated by reference.

BACKGROUND OF THE INVENTION

This invention relates generally to acetabular prosthetic devices and more particularly to an improved acetabular shell liner wherein the liner has a variable geometry rim surface.

Artificial implants, including hip joints, shoulder joints and knee joints, are widely used in orthopedic surgery. The human hip joint acts mechanically as a ball and socket joint, wherein the ball-shaped head of the femur is positioned within the socket-shaped acetabulum of the pelvis. In a total hip joint replacement, both the femoral head and the surface of the acetabulum are replaced with prosthetic devices.

A first general class of hip prosthetic devices included an acetabular component in which the head of a prosthetic femoral component was intended to articulate relative to the acetabular component. Initial designs featured an acetabular component with a thin bearing surface, or liner, which interfaced with a large femoral component head. This design allowed for good range of motion and a low incidence of dislocation or subluxation of the femoral component head, but the thin liners proved to wear poorly, requiring replacement.

Acetabular components generally comprise an assembly of a shell and a liner. The completed acetabular component is configured to be received and fixed within the acetabulum of a pelvis. Generally, a metal shell and a polymeric liner are used to form the component, however, the liner may be made of a variety of materials, including but not limited to, polyethylene, ultra high molecular weight polyethylene, metal, and ceramic materials. Shells may typically be comprised of titanium, stainless steel, cobalt chromium, alloys thereof, or any other appropriate biocompatible material.

Typically the shell has a hemispherical shape and features an outer, convex surface and an inner, concave surface that is adapted to receive the shell liner. The liner fits inside the shell and has a convex and concave surface. It acts as a bearing element in the acetabular component assembly. The convex surface of the liner corresponds to and sits in the inner concave surface of the shell or acetabulum, and the concave surface receives the head of a femoral component.

The internal concave surface of the liner is characterized by features relative to an axis through a center of the concave surface. This axis may or may not be aligned with the central axis of the shell. In a typical liner, the concave surface has a hemispherical geometry and may be referred to as the internal diameter. In such liners, the geometry is characterized by features that are concentric to an axis that runs through the center of the internal diameter.

However, liners may have differing forms and geometries. For example, liners may be made in a one-piece configuration or they may consist of more than one piece. When in place, they may lie flush with the shell opening, they may have portions that extend above the shell opening, or they may completely extend above the shell opening, depending upon the intended use of the liner. The uses and possibilities of various liners and their relation to embodiments of the invention will be described in more detail below.

The femoral component generally comprises a spherical or near-spherical head attached to an elongate stem with a neck connecting the head and stem. It may be a one-piece unit or may comprise a modular or multi-piece unit. In use, the elongate stem is located in the intramedullary canal of the femur and the spherical or near-spherical head articulates in the internal diameter of the liner.

Currently, a hip joint prosthesis may comprise an acetabular component having a thicker liner and a femoral component having a smaller sized head than the initial designs. Acetabular designs that include thicker liners provide more bearing support and less surface area for wear, but they may present problems with dislocation and subluxation, as well as reduced range of motion, due to the smaller head size. Thus, one of the critical concerns in designing total hip joint replacement components is how to design the components to minimize contact of the neck of the femoral component with the rim of the liner during articulation, thus reducing rim contact-induced subluxation, dislocation, and wear, while allowing a maximum desired range of motion. There are a variety of acetabular liners available for use in hip replacement procedures that seek to address the issues of limited range of motion, rim-contact wear, and dislocation or subluxation.

For example, the standard, non-anteverted liner, also called a flat, neutral, or zero degree liner, has a wide rim, or impingement, surface. Typically, the center of rotation of the femoral head on a standard liner is concentric with the acetabular shell. This type of standard liner is used to provide a broad range of motion. Use of this liner requires optimal positioning of the acetabular component in the acetabulum in order to provide the required range of movement for a patient. While standard liners allow a broad range of motion, if malpositioned, they present an increased possibility of dislocation. To address this problem, a high wall liner may be used.

In contrast to standard liners, high wall liners, also known as shouldered, lipped, or elevated liners, employ an extended, elevated portion over a segment of the periphery of the liner internal diameter in order to increase coverage of the femoral head, and thus reduce the likelihood of dislocation and aid in reduction of the head should subluxation occur. The use of high wall liners may be beneficial in cases of tenuous stability in order to avoid dislocation. See e.g. T. Cobb, et al., *The Elevated-Rim Acetabular Liner in Total Hip Arthroplasty: Relationship to Postoperative Dislocation*, Journal of Bone and Joint Surgery, Vol. 78-A, No. 1, January 1996, pp. 80-86.

Another type of liner (that may, in some instances, also be considered a high wall liner) is an anteverted liner. Anteverted liners angle or rotate the central axis of the internal diameter of the liner relative to the central axis of the shell. Anteverted liners shift the contact area on the head of the femoral component in order to improve hip joint stability and decrease the risk of dislocation. However, use of an anteverted liner may reduce allowed range of motion.

Another type of liner that may be used to prevent recurrent dislocation in a high risk patient is a constrained liner. This type of liner has an elevated portion over the entire periphery of the liner internal diameter. The elevated rim can reduce the chance for dislocation or subluxation of the femoral implant, but can also limit its range of motion. In short, high wall liners of all designs (including anteverted and constrained liners) may reduce the arc of motion to contact in the direction of the elevated rim segment without a corresponding increase in motion in the opposing direction. Thus, there is a substantial loss of overall range of motion compared to a standard (or flat or zero degree) liner. This reduction in range of motion makes the rotational positioning or clocking of these designs in the acetabulum particularly important in order to reduce rim contact with the neck of the articulating femoral component and potential acceleration of polyethylene wear at the rim as a result of this contact.

In general, a liner has a rim where the inner surface meets the outer surface of the liner. The rim may be in the form of an edge, a chamfer, a radius, or a surface. Some of the available liners have a constant geometry relieved rim surface around the circumference of the internal diameter of the liner. While a relieved rim surface increases range of motion, the constant geometry may not optimize the possible range of motion because it may not be correlated to the cross-section of the femoral component during a condition of femoral component neck-liner contact. At this point, the femoral component is said to be in an impingement condition with the liner.

Prosthesis range of motion has been evaluated in the past by creating a cone that defines the limits of motion to contact, or impingement angles, for the prosthesis, as described in Thornberry, et al., *The Effects of Neck Geometry and Acetabular Design on the Motion to Impingement in Total Hip Replacement*, A Scientific Exhibit at the 1998 AAOS Meeting, New Orleans, La., 1998, the entire contents of which are hereby incorporated by reference. The size of the cone depends on the design of the components. Varying the orientation of the components allows a surgeon to shift the direction of the cone. In a successful component placement, the cone is positioned so that adequate range of motion for the patient is provided. The base of the cone provides information for flexion, extension, adduction, and abduction. The direction of flexion-extension, as well as abduction-adduction, can be drawn as a line on the base of the cone. The point where the line intersects the cone is the maximum motion of prosthesis in the respective direction. Designs that provide adequate range of motion generally correlate with good clinical results. See e.g. B. McGrory, et al., *Correlation of Measured Range of Hip Motion Following Total Hip Arthroplasty and Responses to a Questionnaire*, Journal of Arthroplasty, Vol. II, No. 5, 1996.

Thus, there is a need for a method of forming an acetabular shell liner that provides optimization of the maximum range of motion and minimum interference with the femoral component neck. There is a further need for a constrained liner that can limit the possibility for dislocation, but also provide a greater range of motion and limit impingement of the femoral component. There is a further need for methods that can be used to form such liners.

BRIEF SUMMARY OF THE INVENTION

Methods and structures according to this invention include constrained liners and methods of producing constrained liners in which the rim surface geometry varies, rather than being set, in order to optimize the range of motion and minimize interference with the neck of the femoral component. This variable geometry rim surface is employed around the edge of the internal concave surface of the liner, where the opening meets the rim, and in some instances, at the edge of the portion of the liner that extends beyond the shell, and allows for delayed interference, or impingement, with the neck or stem portion of the femoral component, resulting in an increased range of motion. Thus, this variable geometry rim surface delays when the neck of the femoral component contacts the rim surface of the liner during articulation, allowing an increase in the range of motion of the femoral component and optimization of the liner.

Increasing the range of motion has many clear benefits and advantages. First, it allows a patient a greater range of movement. Second, an increase in the range of motion provides the surgeon with greater room for error in component positioning, or clocking, during surgery. Because it is not currently possible to accurately measure the precise angle required for implantation of an acetabular component in a particular patient, it is difficult to place an implant at precisely the correct angle. A surgeon generally relies on personal experience in making this assessment. While a locking mechanism, such as a spline interface between the liner and the shell, is beneficial because it allows for multiple reorientations of the liner, fine tuning the positioning of the acetabular component during the intraoperative assessment of range of motion and stability is difficult and often imprecise. Surgeons will benefit from a wider range, or larger target area for acetabular component orientation provided by the increased range of motion.

Third, a broader range of motion decreases the likelihood of dislocation or subluxation, as it is less likely the femoral component will contact the rim of the liner and lever out of the internal concave surface of the acetabular component. Finally, a broader range of motion aids in preventing wear on the liner or shell. If a femoral component regularly contacts the rim surface of the liner, the liner will wear, releasing polyethylene debris. This debris may cause osteolysis when it escapes into nearby bone and tissue, which may lead to aseptic loosening of the implant. Additionally, if the liner wears thin, the neck of the femoral component may contact the metal shell, resulting in fatigue to the metal that may cause the neck or shell to break, or metal debris to be released into nearby bone and tissue.

These and further advantages of the present invention will become apparent after a review of the following detailed description of the disclosed embodiments.

Some aspects of embodiments of the invention relate to a constrained liner, comprising:

(a) an internal concave surface having an opening adapted to receive a head of a femoral component, wherein the internal concave surface provides greater than hemispherical coverage of the head;

(b) an external surface positioned on an opposing side of the internal concave surface;

(c) a rim located at the opening of the internal concave surface, the rim comprising a variable angle chamfer surface, wherein the variable angle chamfer surface allows the constrained liner to receive a head of a femoral component and help prevent dislocation, while also providing a greater range of motion than that provided by a constrained liner without a variable angle chamfer surface.

Other aspects relate to a prosthetic device comprising an acetabular shell comprising an internal concave surface adapted to receive a constrained liner and an external surface adapted to be received in an acetabulum; and the constrained liner described above.

Further aspects relate to a method of making a constrained liner with a variable rim surface geometry comprising:

(a) providing a constrained acetabular liner comprising an internal concave surface adapted to receive the head of a femoral component, an external surface positioned on an opposing side of the liner, and a surface generally defining at least a part of a rim of the liner, said surface located between the internal concave surface and an external surface of the liner;

(b) rotating a femoral component in the constrained liner to define a radial location on the rim of the liner where the femoral component impinges on the rim and noting that radial location;

(c) defining the impingement angle of the femoral component on the rim at this radial location and noting that impingement angle;

(d) defining the location and desired shape of a cross-sectional rim segment at that impingement angle and radial location, based at least in part on the cross-sectional shape of the portion of the femoral component that is in an impingement condition with the liner, and noting that location and desired shape of the cross sectional rim segment;

(e) rotating the femoral component in the constrained liner to define a separate radial location on the rim where the femoral component impinges on the rim and noting that radial location;

(f) repeating (c)-(e) as desired; and (g) forming the constrained liner with a variable geometry rim surface using the data obtained in steps (b)-(f), whereby the shape of the liner rim varies at a plurality of radial locations in a manner corresponding to the cross-sectional shape of the portion of the femoral component that is in an impingement condition with the liner.

Even further aspects relate to a method of replacing a hip joint in a patient comprising:

(a) providing an constrained liner having:
   (i) an internal concave surface having an opening adapted to receive a head of a femoral component, wherein the internal concave surface provides greater than hemispherical coverage of the head;
   (ii) an external surface positioned on an opposing side of the internal concave surface;
   (iii) a rim located at the opening of the internal concave surface, the rim comprising a variable angle chamfer surface, wherein the variable angle chamfer surface allows the constrained liner to receive a head of a femoral component and help prevent dislocation, while also providing a greater range of motion than that provided by a constrained liner without a variable angle chamfer surface;

(b) providing an acetabular shell comprising an internal concave surface adapted to receive the liner and an external surface adapted to be received in an acetabulum;

(c) surgically implanting and securing the shell in the acetabulum of a patient;

(d) securing the liner in the internal concave surface of the shell;

(e) providing a femoral component, comprising a head, neck and a stem, wherein the head is adapted to articulate within the internal concave surface of the liner;

(f) surgically implanting the stem of the femoral component into the femur of a patient; and (g) installing the head of the femoral component into the internal concave surface of the liner.

BRIEF DESCRIPTION OF SEVERAL VIEWS OF THE DRAWINGS

FIG. 10 shows the assembly of a two-piece constrained liner, with a bearing portion being inserted into a shell.

FIG. 11 shows the completed assembly of FIG. 10.

FIG. 16 shows the assembly of a one-piece constrained liner being inserted into a shell.

FIG. 17 shows the completed assembly of FIG. 16.

DETAILED DESCRIPTION OF THE INVENTION

Figure 1:
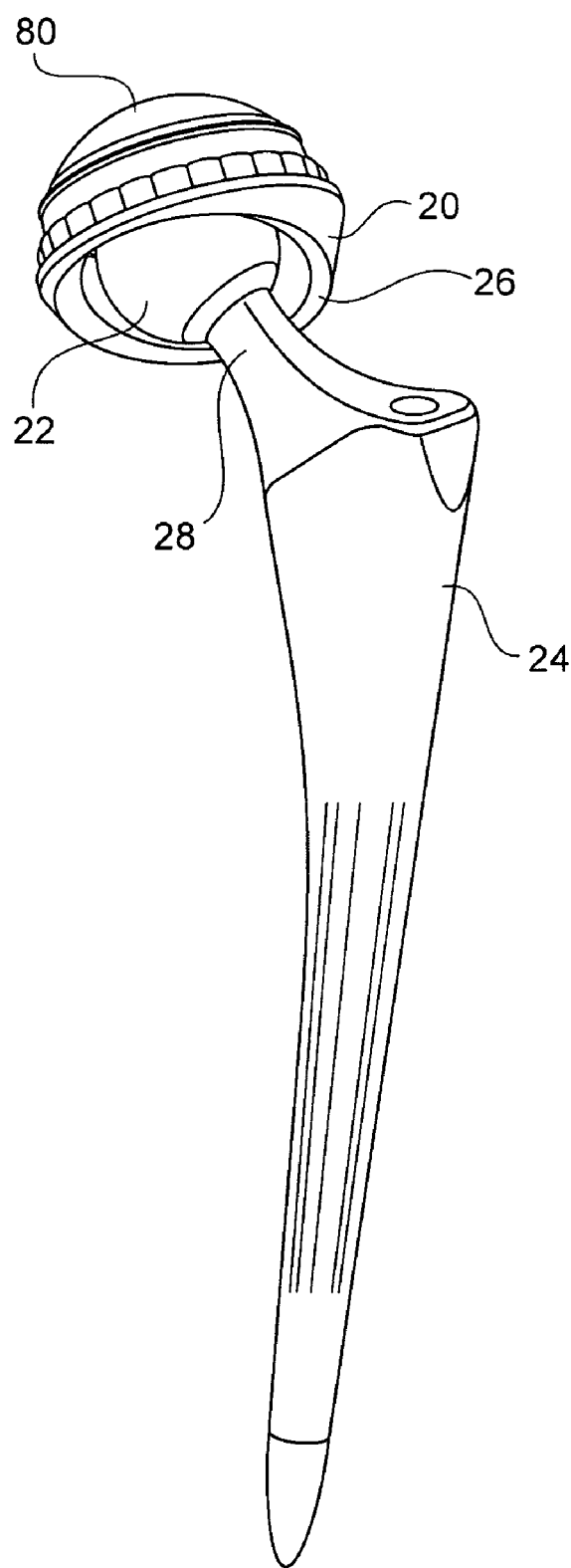
FIG. 1 is a perspective view of a femoral component and constrained liner of a hip prosthesis according to one embodiment of the invention.

Methods and structures according to this invention seek to improve the range of motion of the femoral component of a hip prosthesis by varying the rim surface geometry of the rim of an acetabular shell liner in which the femoral component articulates, and particularly the rim geometry of a constrained liner. Varying the geometry of the rim surface relative to the internal concave surface opening or axis of the liner at different areas on the liner allows for optimization of the rim surface geometry, thus providing an increased range of motion. Liners with variable angle chamfer surfaces according to various embodiments of this invention have an overall range of motion generally at least comparable to a conventional constant geometry rim surface constrained liner.

Optimization of the acetabular shell liner rim surface geometry takes consideration of many elements in the design of the liner, including, but not limited to, range of motion of the femoral component, rotational stability of the femoral component, mechanical integrity, locking strength between the liner and the shell, material thickness constraints, as well as other considerations. All of these factors should be balanced in designing an optimized constrained liner, including the variable geometry rim surface. Thus, changing the geometry of a liner to obtain the best possible range of motion is impacted by other design constraints.

While use of a constrained liner is not always desirable due to resulting decreased range of motion, it is necessary in some patients who are repetitive dislocators. Thus, although helpful in limiting dislocation, constrained liners are typically indicated when other treatment methods are not effective (e.g., in instances where there is significant extremity shortening, multidirectional instability, or recurrent instability following revision) because they limit the range of motion provided by the hip replacement surgery. However, providing constrained liners with a variable angle chamfer according to various embodiments of this invention can help increase the range of motion that the constrained liner provides. This feature may help overcome one of the primary downsides of the use of constrained liners—limited range of motion—and may allow constrained liners to be more viable options.

As used herein the term "internal concave surface" refers to the internal concave surface of the liner that receives a femoral component head. The internal concave surface may be hemispherical, oval, elliptical, oblong, or any other generally concave geometric shape. The term "internal diameter" refers to the internal concave surface of a liner; it may be partially spherical, hemispherical, or less or more than hemispherical. "External diameter" refers to an external surface opposing the internal concave surface and is adapted to be received in an acetabular shell or directly into the acetabulum of a patient. The term "articulation bearing surface" refers to the portion of the internal concave surface in which the head of the femoral component articulates or moves in a manner corresponding to motion of the femur relative to the acetabulum.

The term "rim" or "rim surface", as used herein, refers to a surface of the liner located generally between the internal concave surface and an external surface of the liner. "Sculpted surface," "variable angle chamfer," or "variable angle surface" means a surface which forms at least part of the rim of the liner and that varies around the rim of the liner according to the orientation of the femoral component at the outer limits of its range of motion.

Liners according to this invention may include a family of variable geometry rim surface acetabular liners having differing sizes, with each size having different rim surface geometries. Each of the outer diameters of the liners gets progressively larger with each increasing size, corresponding to the size of the acetabulum. As the size increases, the rim surface angle, or chamfer angle, can widen, or become more or less obtuse as a general matter. Moreover, the size of the shell typically corresponds to the size of the liner.

An example of a liner 20 receiving a femoral component 24 is shown in FIG. 1. Liner 20 has an internal concave surface 50 (shown more clearly in FIG. 2) that is adapted to receive the head 22 of a femoral component 24, an external surface 52 positioned on an opposing side of the liner from the internal concave surface, and a sculpted surface or variable angle chamfer surface 26 defining at least part of a rim 54 of the liner, which has a variable angle that changes or varies around the rim of the liner. The rim 54 (which is the surface that defines the outer limits or extent of the range of motion) is the surface of the constrained liner 20 that restricts the rotation of the femoral component 24. One example of a possible rim surface geometry is the chamfer 26. One reason a chamfer, curve, or other rim surface, is used is to increase the range of motion of the femoral component.

Figure 2:
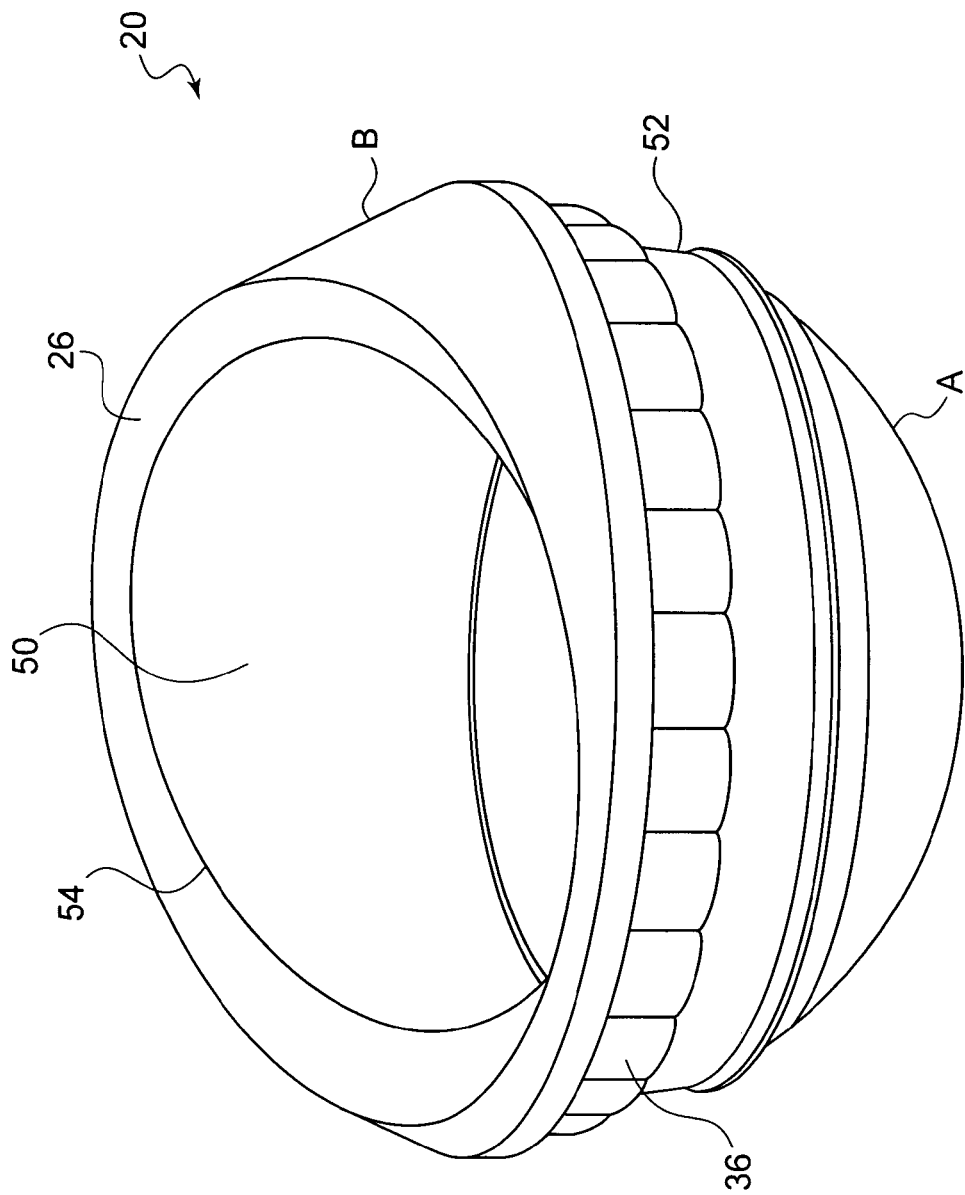
FIG. 2 is a perspective view of a two-piece constrained liner having a variable angle chamfer surface according to various embodiments of the invention.
Figure 3:
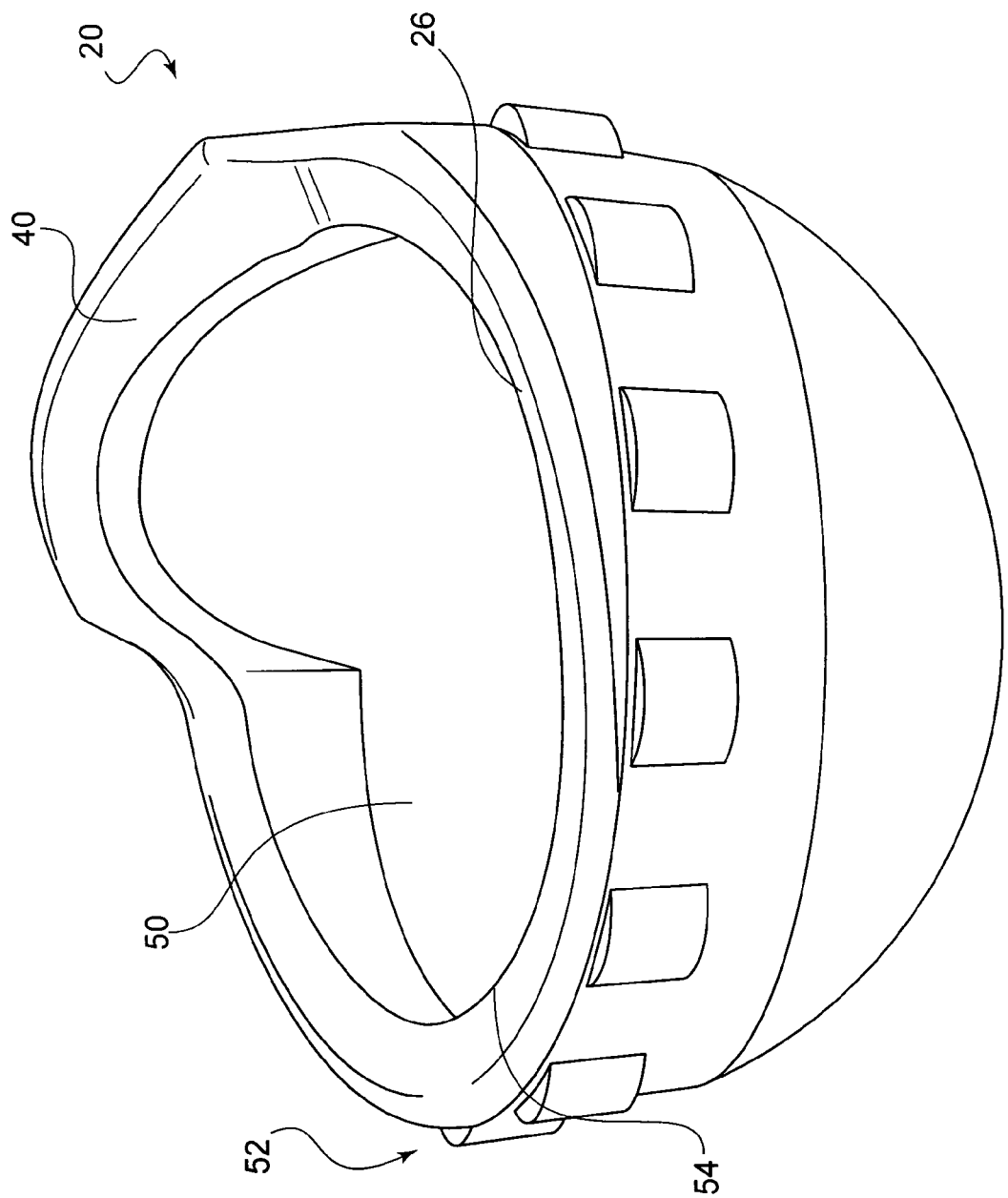
FIG. 3 is a perspective view of a one-piece constrained liner having a variable angle chamfer surface according to various embodiments of the invention.

FIGS. 2-9 show examples of these types of constrained liners according to various embodiments of the invention. The figures show one and two-piece liners. The liners 20 are shown having a greater than hemispherical configuration, meaning that they provide greater than 180 degrees coverage of a femoral head received by the liner 20. As shown in FIGS. 2-3 and detailed more in FIG. 4, the geometry of the rim surface is a variable chamfered surface 26 at the rim portion 54 where the internal concave surface 50 of the liner and the external surface 52 of the liner meet. FIG. 2 shows a two-piece constrained liner that has been assembled without the femoral head in place. The liner has two components, A and B. The components may be placed together and secured using any appropriate system or method, such as a snap locking ring, a wire, or any other method. Liner is shown having serrations or anti-rotations tabs 36, which can cooperate with corresponding indents on the shell (as shown in FIG. 10).

FIG. 3 shows a one-piece constrained liner. It also has a variable chamfered surface 26 at the rim portion 54 where the internal concave surface 50 of the liner and the external surface 52 of the liner meet. The one-piece liner may also have a hood member 40 that extends above the remainder of the rim 54. This feature is shown and described in more detail in FIGS. 16-22, but in short, hood member 40 helps to constrain head 22 in place during use.

Figure 4:
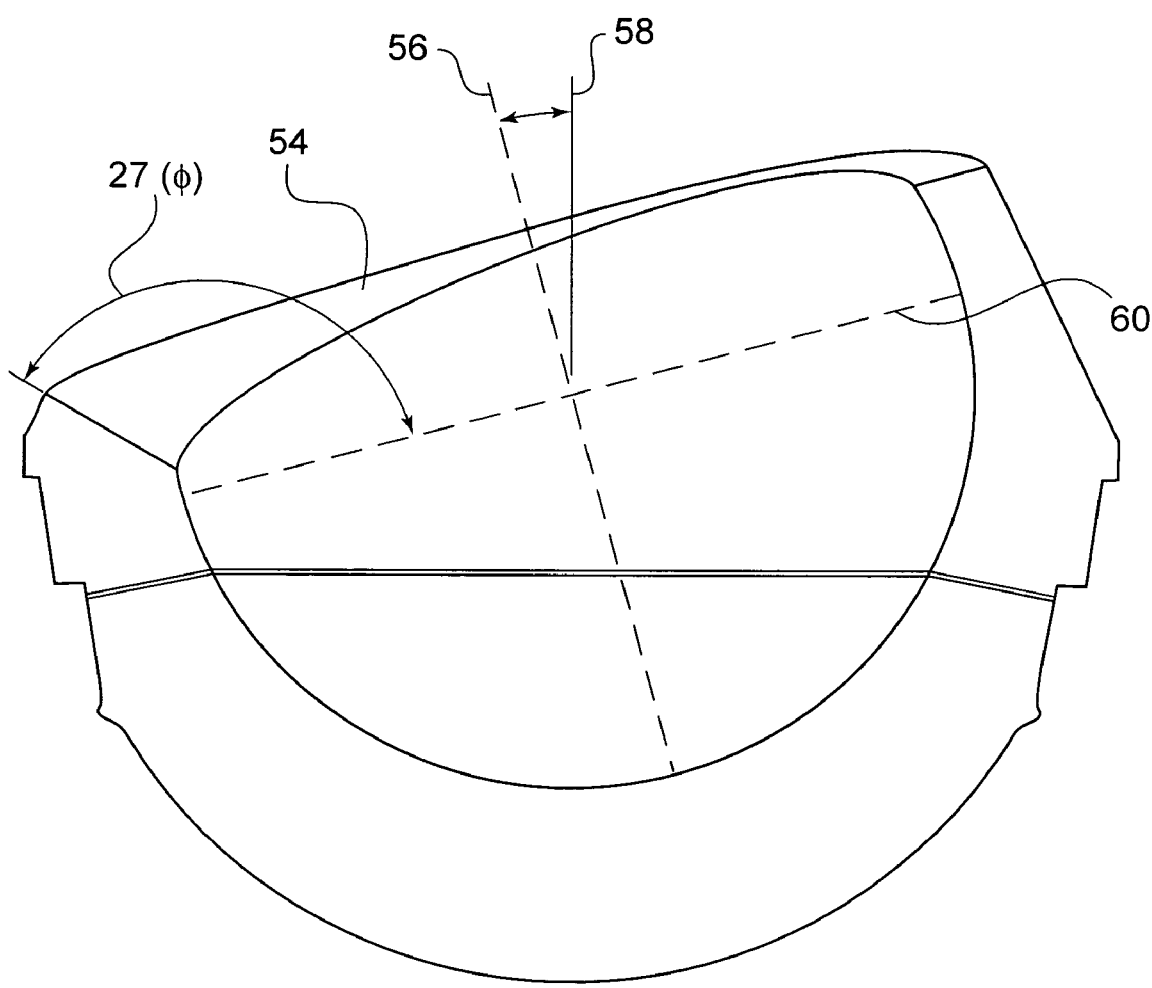
FIGS. 4 and 6 are views showing potential rim angle variations for the variable angle chamfer surface of a two-piece liner at different areas along the rim.
Figure 5:
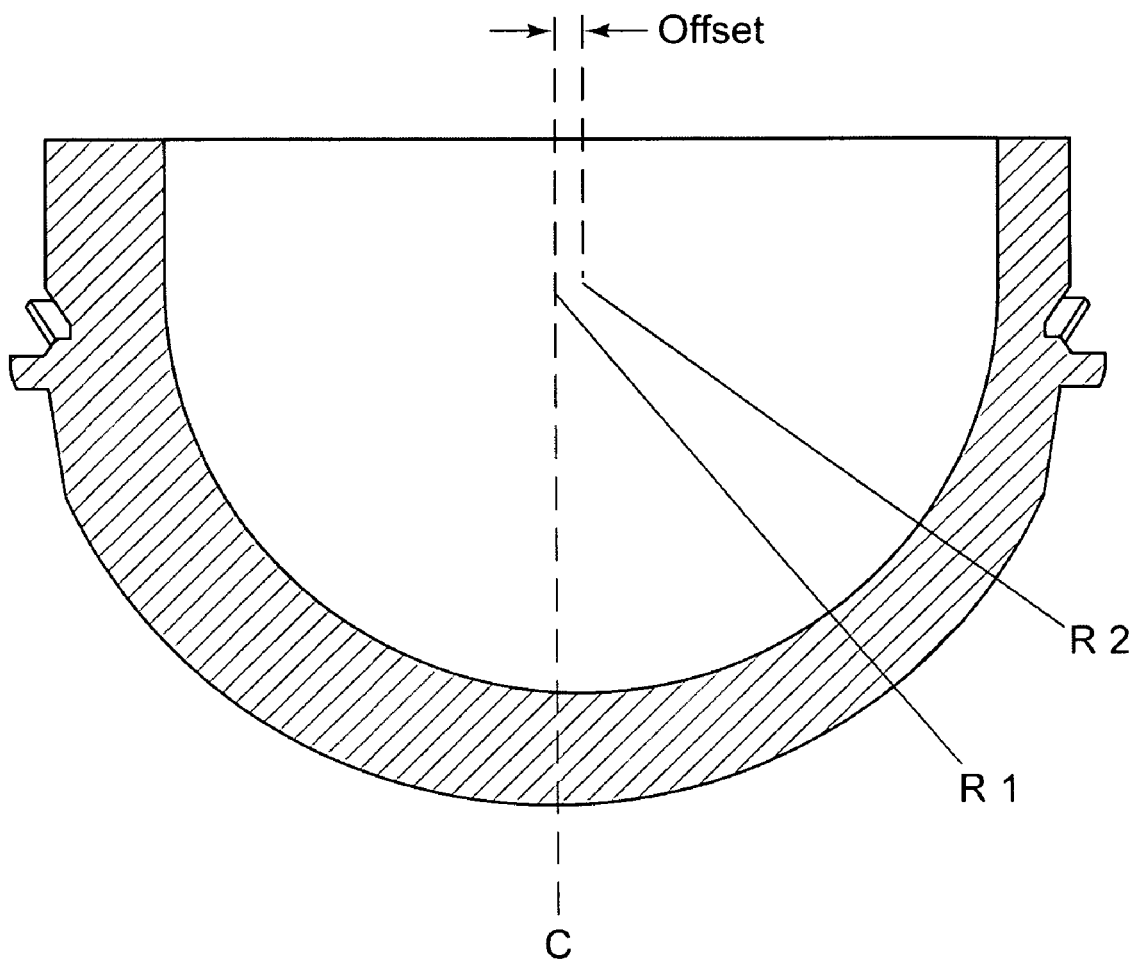
FIG. 5 shows a cross-sectional side view of an offset liner.

As shown in FIG. 4, the center axis 56 of the constrained liner internal diameter may be angled relative to the center axis 58 of the shell in any direction and at any angle, i.e., it may be provided as an anteverted liner. The center axis 56 of the internal diameter 50 of the liner (e.g., the liner axis) may be angled or rotated at a range from about 1 to about 45 degrees, more particularly from about 10-45 degrees, more particularly from about 10-30 degrees, and most particularly, from about 15-20 degrees relative to the central axis 58 of the shell (or other surface in which the liner is adapted to be received). As an example, the center axis 56 of the internal diameter 50 of the liner may be angled or rotated at 15 degrees. It should also be understood that it is also possible for the axes to be offset or shifted relative to one another. An example is shown in FIG. 5, where a first radius "R1" is that radius at the centerline of the shell "C", and the second radius "R2" is the radius of the offset liner. Although such embodiments are considered within the scope of this invention, they will not be discussed further, and the axis angle referred to above is a rotation of the liner axis 56 relative to the central axis 56 of the shell. It is also possible for the center axis 56 of the constrained liner internal diameter to align with the center axis 58 of the shell. In other words, constrained liners according to various embodiments may be anteverted, neutral, or offset. The entire rim 54 of the liner extends beyond a phantom hemispherical line 60 so that a femoral head 22 is captured by the liner 20 completely.

Liner 20 has variable angle chamfer 26, which chamfer angle 27 ($\phi$) varies in order to optimize the range of motion of femoral component 24 with respect to other structural variables. In these figures, the chamfer angle 27 is defined as the angle at any point on or near the periphery of the liner internal diameter 50 at which the surface of the chamfer 26 is positioned relative to the center axis 56 of the opening of the internal diameter of the liner, about which the femoral component stem articulates. For example, as shown in FIG. 6, variable chamfer angles ranging from 135-180 degrees are shown, although it is understood that other angles may be chosen depending upon the size of the geometry of the components, the desired range of motion, and other variables.

Figure 6:
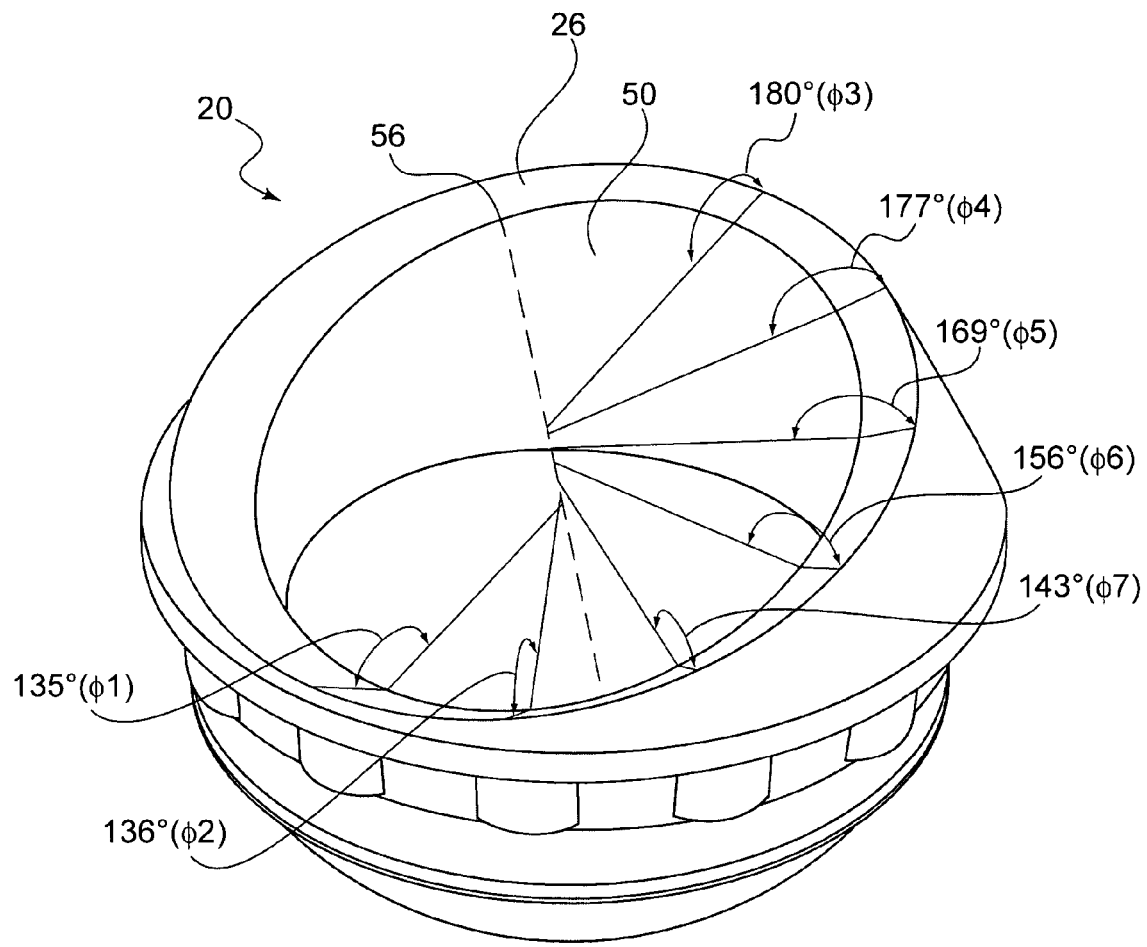
Figure 7:
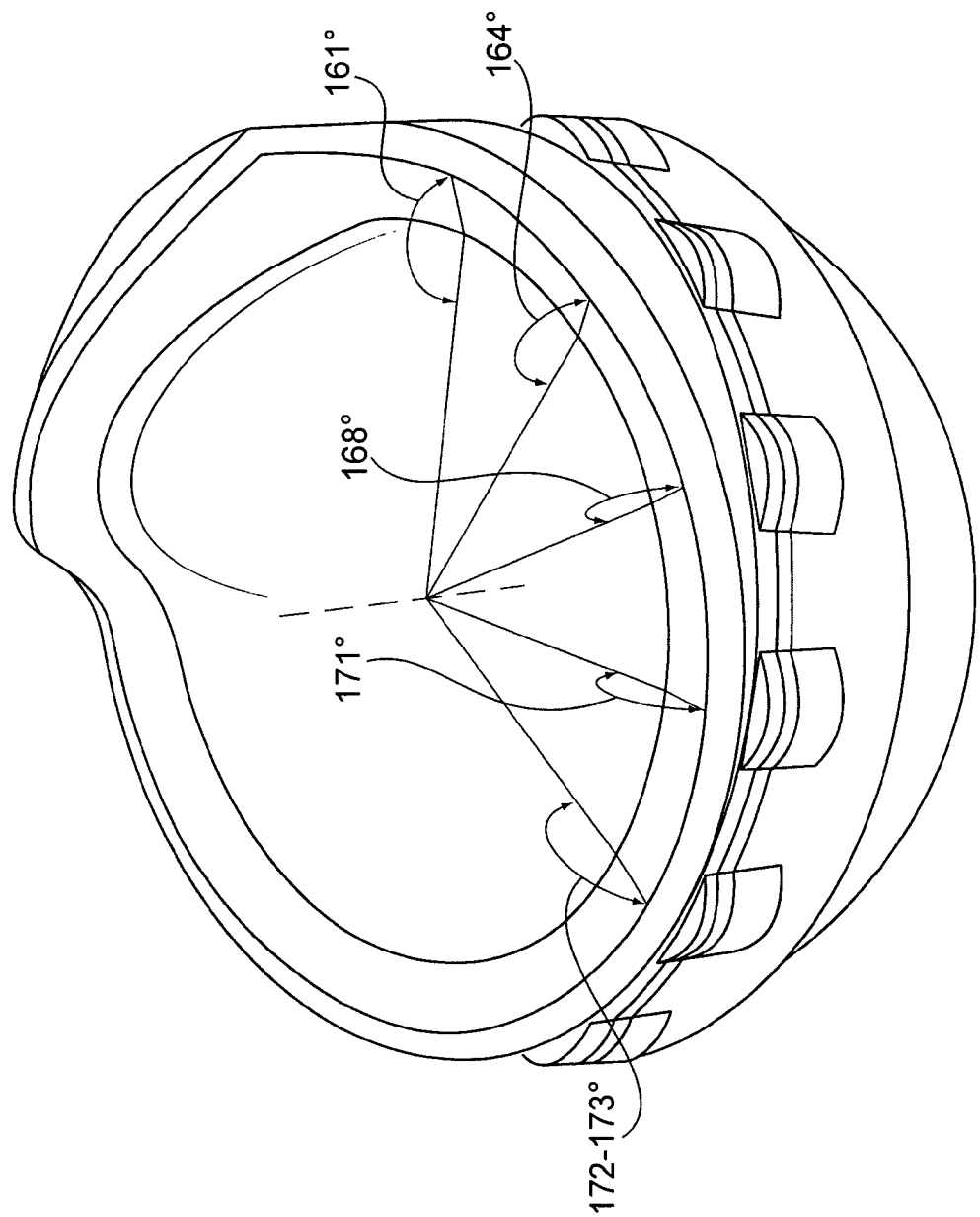
FIG. 7 is a view showing potential rim angle variations for the variable angle chamfer surface of a one-piece liner at different areas along the rim.

Thus, in this embodiment, the angle between the liner axis 56 and any point of the periphery of the internal diameter 50 is a variable chamfer angle (ϕ) (shows as ϕ1-ϕ7 in FIG. 6). It should be understood, however, that the variable angle may be defined relative to any other reference line or plane defined by the structure of the liner, such as the center axis or an axis of rotation of the inner diameter, the center axis or axis of rotation of the external, or outer, diameter, or some other reference entity. Another example showing variable chamfer angles for a one-piece liner is shown in FIG. 7. These angles are shown as ranging from 161-173 degrees, although again, it is understood that other angles may be chosen depending upon the size of the geometry of the components, the desired range of motion, and other variables. In another embodiment, the plurality of variable angles range from about 100 degrees to about 200 degrees.

Figure 8:
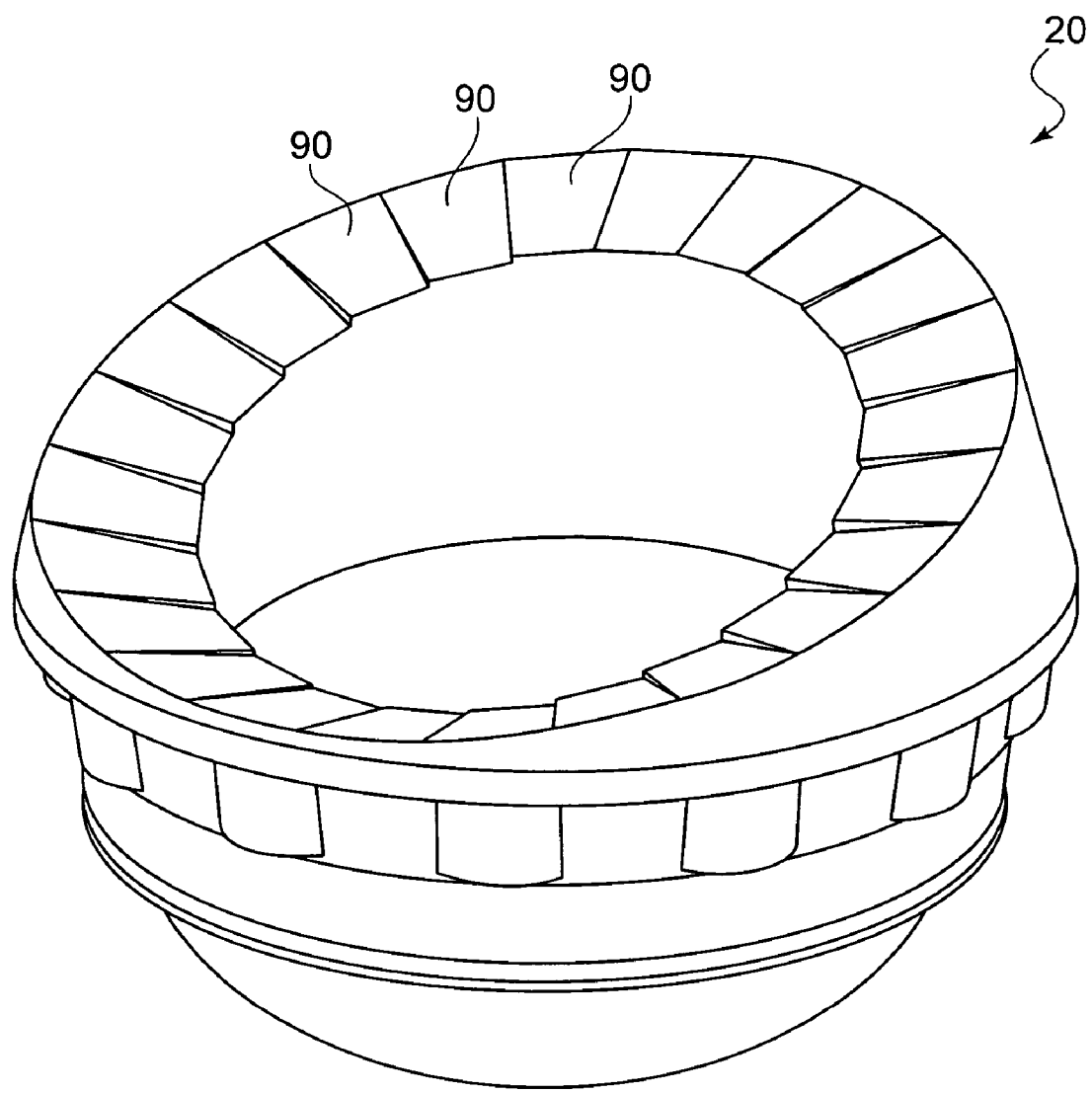
FIG. 8 shows an embodiment of the invention having a divided rim surface in which the rim surface of the constrained liner is divided into several constant angle sections so as to approximate a single varying angle rim surface.
Figure 9:
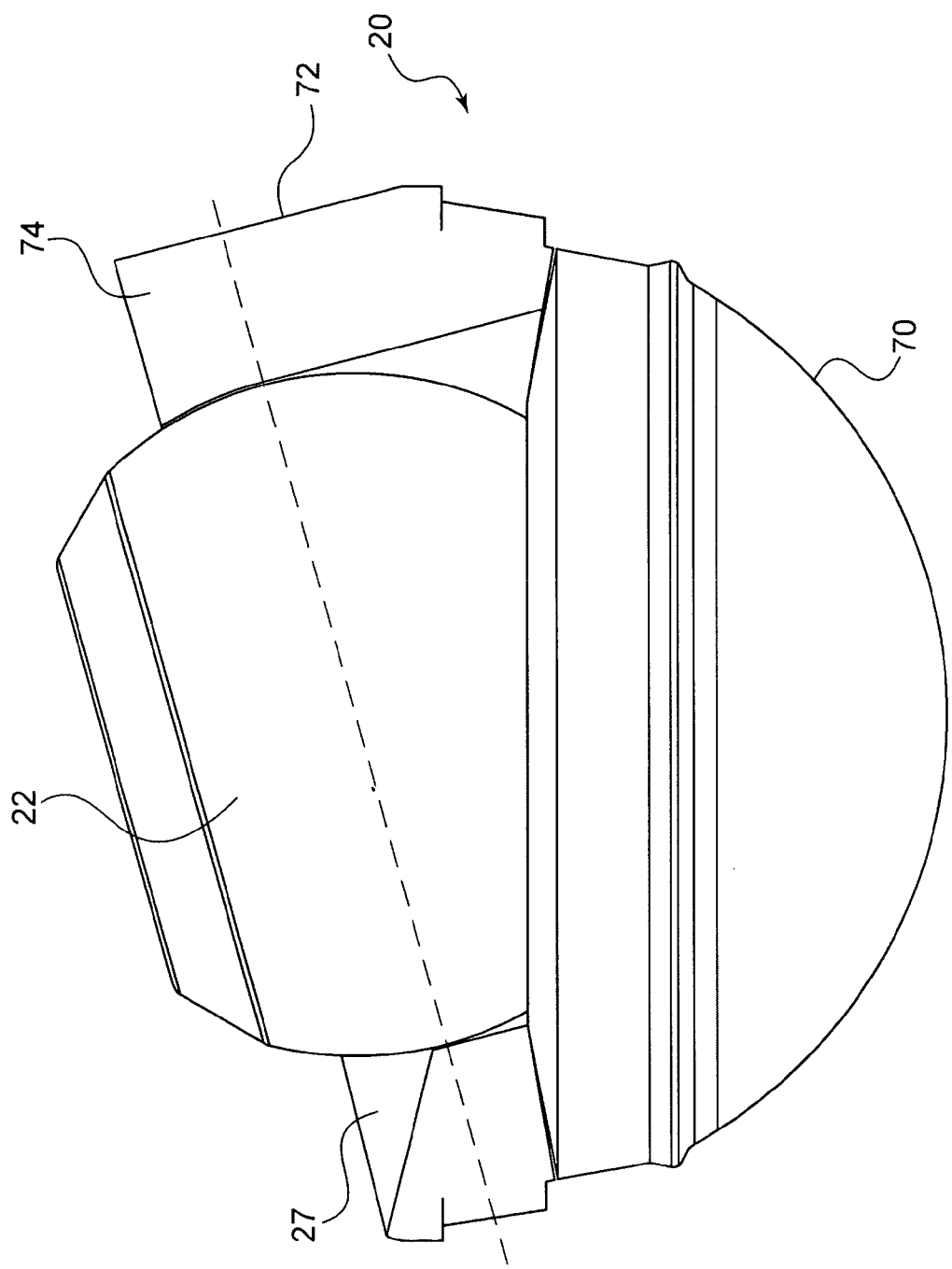
FIG. 9 is a partial cross-sectional view of a constrained liner that is receiving a femoral head.

Another embodiment of the invention is a divided rim surface in which the rim surface of the constrained liner is divided into several constant angle sections so as to approximate a single varying angle rim surface. An example of this embodiment is shown in FIG. 8. The constant angle sections as shown as reference numeral 90. Another option is to provide the segments as a plurality of variable angle segments.

In another embodiment, the geometry of the rim surface varies around the rim of the liner and is symmetric about a plane, i.e. the reflection about the plane is a mirror image. In other words, the surface may vary around the rim of the liner and may be symmetric or asymmetric about a plane.

As shown in FIG. 1, femoral head 22 and liner 20 act as a ball and socket joint. The contact during articulation of the femoral component neck 28 with liner 20 can be minimized by varying the angle 27 of chamfer 26 to allow neck 28 a broader range of motion prior to contact with liner 20. In the example shown in FIG. 1, neck 28 of femoral component 24 has a circulotrapezoidal (such as a rounded, generally rectangular) cross-section. As the femoral component 24 is rotated, the periphery of the neck 28 limits the rotation of the femoral component 24 relative to the liner 20 because contact of the neck 28 with the chamfer 26 stops rotation of the femoral component. This cooperation is also shown in FIGS. 15 and 22, discussed in more detail below.

Figure 12:
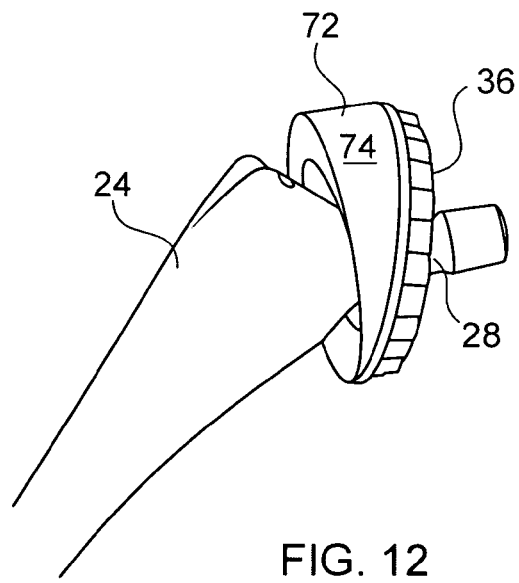
FIG. 12 shows a femoral component stem with a constraining component, prior to assembly.
Figure 13:
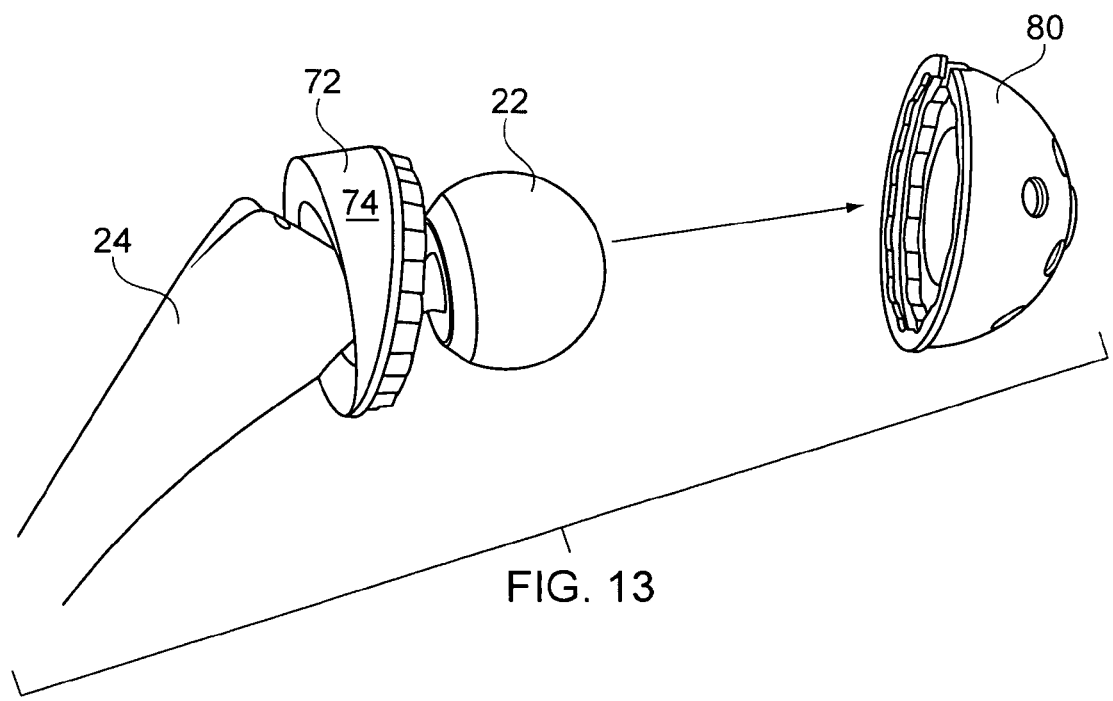
FIGS. 13 and 14 show a stem, a head, and constraining component combination, as it is being inserted into the assembly of FIG. 11.
Figure 14:
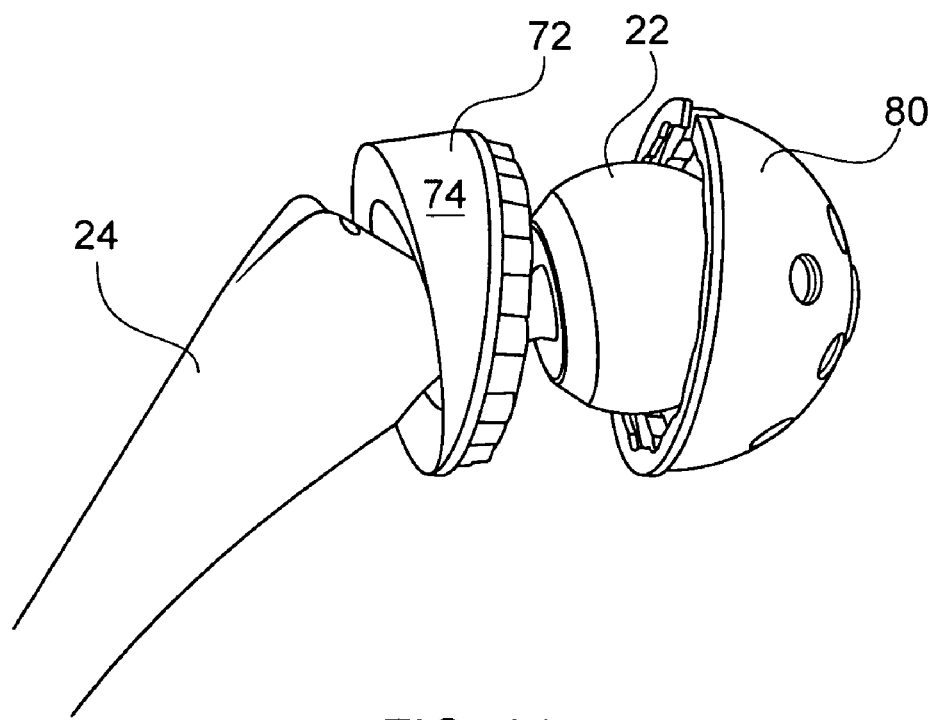

FIGS. 9-15 are useful to illustrate the assembly of a two-piece liner embodiment. As discussed, a constrained liner may be a one-piece liner or a multi-piece liner. In some multi-piece constrained liners, there is a first portion 70 that fits into an acetabular shell 80 (see FIG. 10), and a second portion 72 that extends beyond the entire periphery of the shell and secures the femoral head into the liner (see FIGS. 12-14). The first portion 70 may be a bearing component, and the second portion 72 may be referred to as a locking or constraining component 74. In use, once first portion 70 is in place in shell 80 as shown in FIGS. 10 and 11, second portion may be placed over femoral neck 28 and head 22 is then attached, as shown in FIGS. 12 and 13. The anti-rotation tabs 36 allow second portion 72 to secure with respect to shell 80. The serrated edges of tabs allow liner 20 to interface with an acetabular shell 80. Each spline angle of the serration is shown as being about 15 degrees, thus, the liner can be oriented at 15 degrees all around and adapted to be locked in place in shell. However, it should be understood that the spline angles may be altered as appropriate and that other types of interface may also be employed. For example, the angle depends on how many anti-rotation tabs are used. In some embodiments, there are 12 anti-rotation tabs that are 30 degrees apart, in others there are 18 tabs that are 20 degrees apart, and so forth. Any desired combination is possible.

Figure 15:
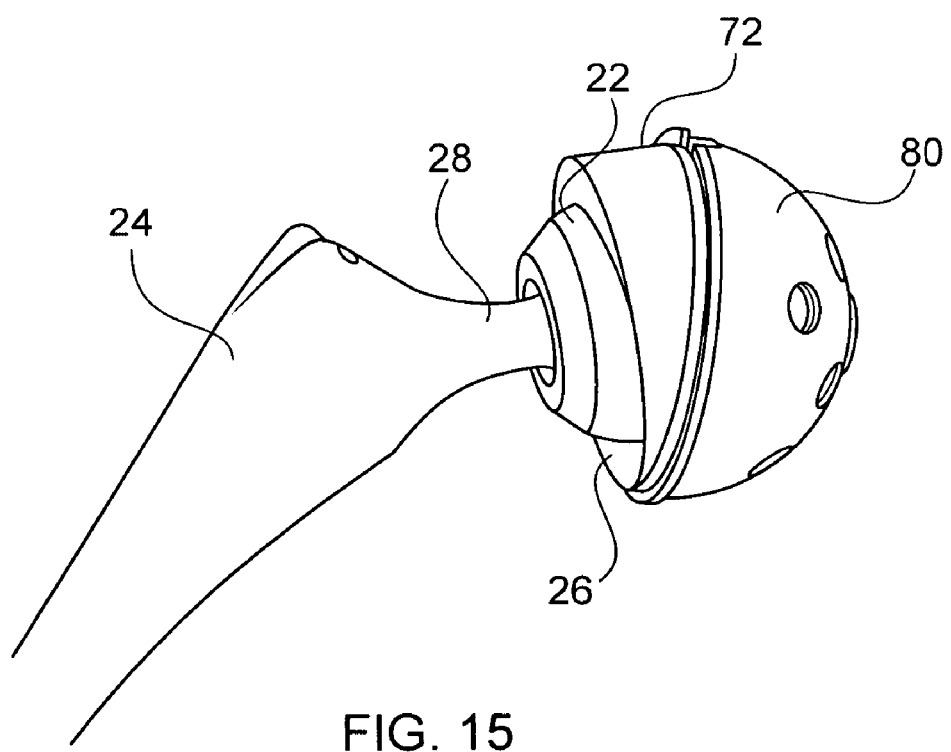
FIG. 15 shows the completed assembly of FIG. 14

Because the femoral implant 24 contacts component 74 during movement (as shown in FIG. 15), there may be instances when the component experiences fatigue fracture due to chronic impingement of the constraining component against the neck of the femoral component. Accordingly, providing the component 74 with a variable angle chamfer 26 can provide a greater range of motion for the femoral component 24, as well as help to limit impingement of the femoral component. FIG. 15 shows a completed assembly, with the variable angle chamfer surface 26 providing a greater range of motion for the femoral head 22 and stem neck 28.

Figure 18:
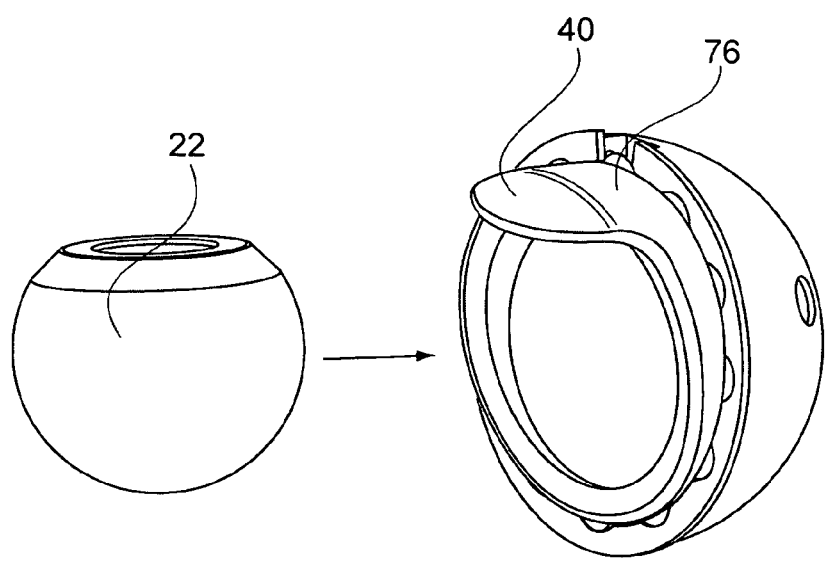
FIG. 18 shows a head and a one-piece liner.
Figures 19, 20:
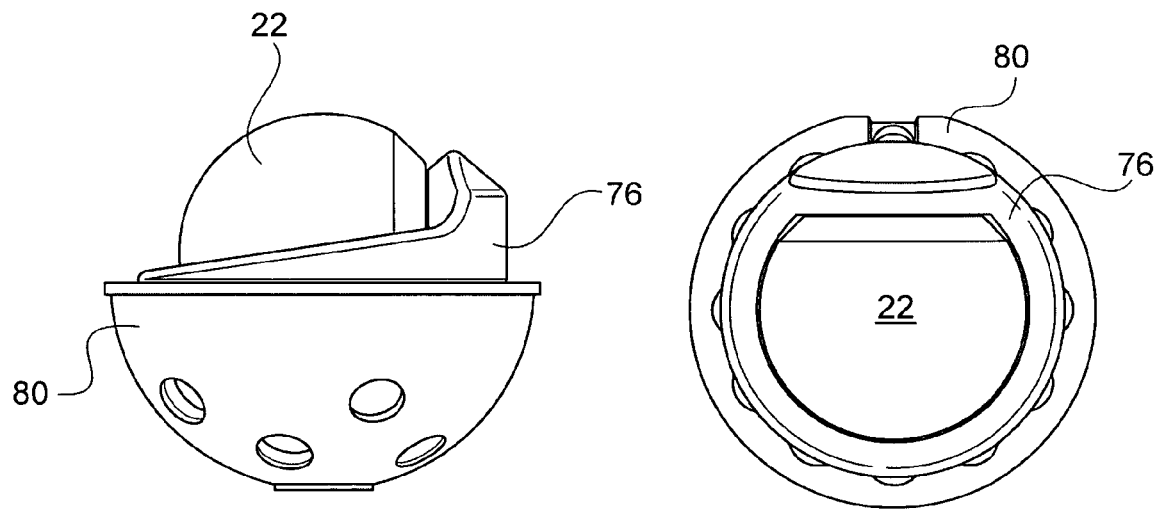
FIG. 19 shows a side perspective view of the head of FIG. 18 inserted into the one-piece liner of FIG. 18.
FIG. 20 shows a top plan view of the assembly of FIG. 19.
Figure 21:
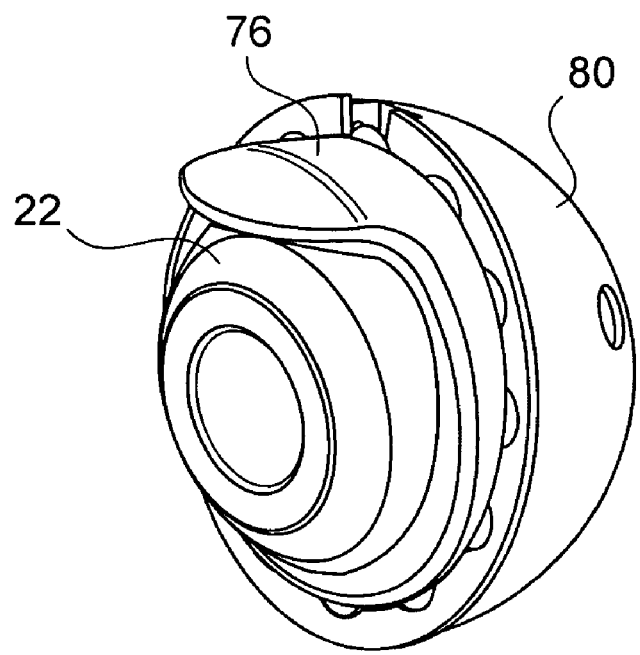
FIG. 21 shows the assembly of FIG. 20 with the head rotated to receive a femoral component stem.
Figure 22:
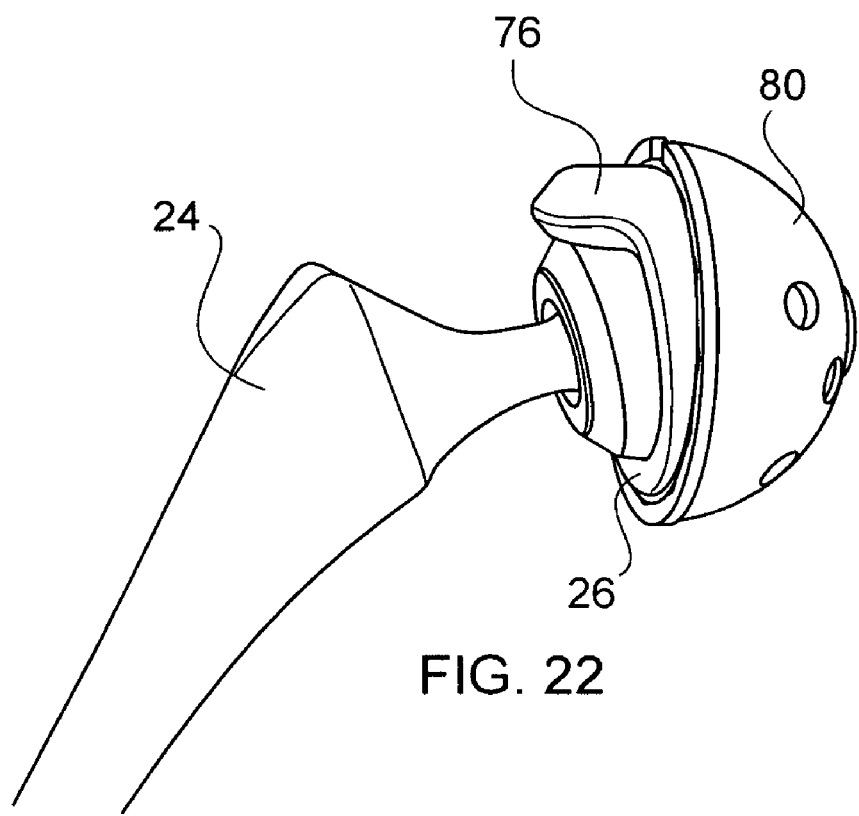
FIG. 22 shows the assembly of FIG. 21 in connection with a stem.

FIGS. 16-22 are useful to illustrate the assembly of a one-piece liner embodiment. The one-piece liner is shown as component 76. Component 76 fits into an acetabular shell 80 (see FIGS. 16 and 17). As shown in FIG. 18, in order to insert head 22, the head is turned so that its flat surface aligns with hood member 40 of component 76. Once in place as shown in FIGS. 19 and 20, head 22 is rotated outward so that it can receive the femoral component stem, as shown in FIGS. 21 and 22. Again, because the femoral implant 24 contacts component rim during movement, the rim can experience fatigue fracture due to chronic impingement. Accordingly, providing component 76 with a variable angle chamfer 26 can provide a greater range of motion for the femoral component 24 and help to limit impingement of the femoral component.

Figure 23:
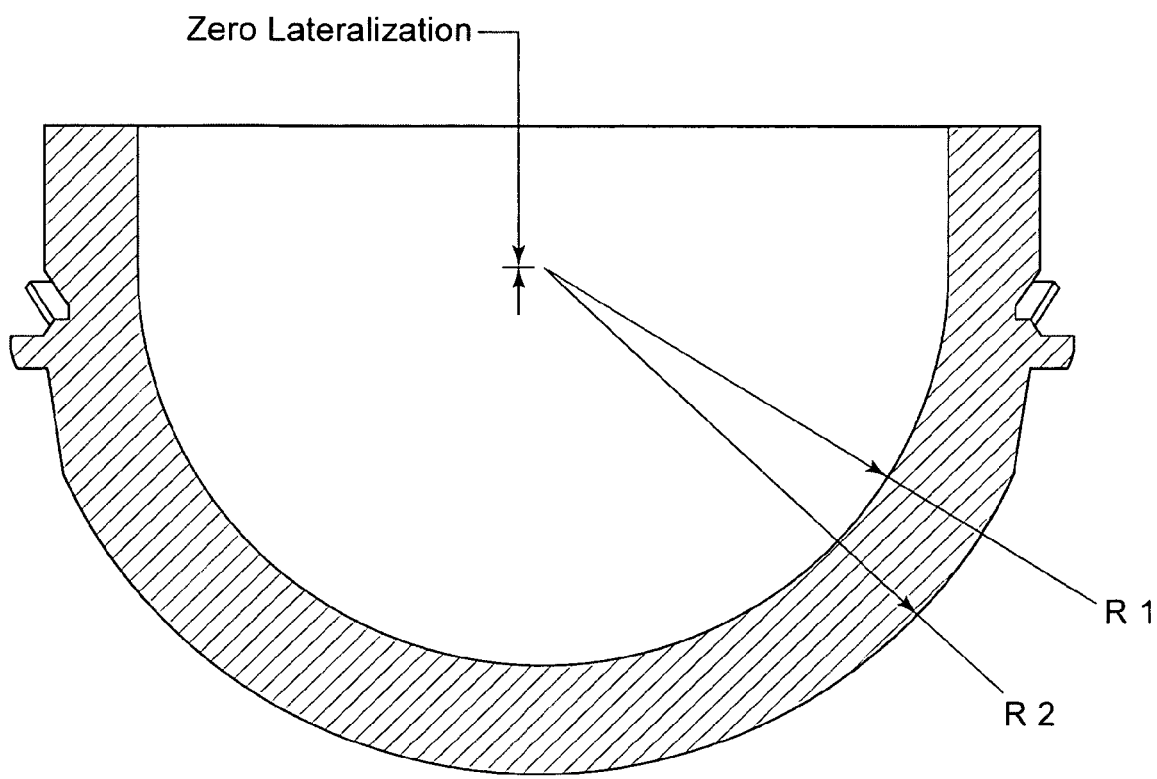
FIGS. 23 and 24 show a comparison of a liner without lateralization and a liner that is lateralized.
Figure 24:
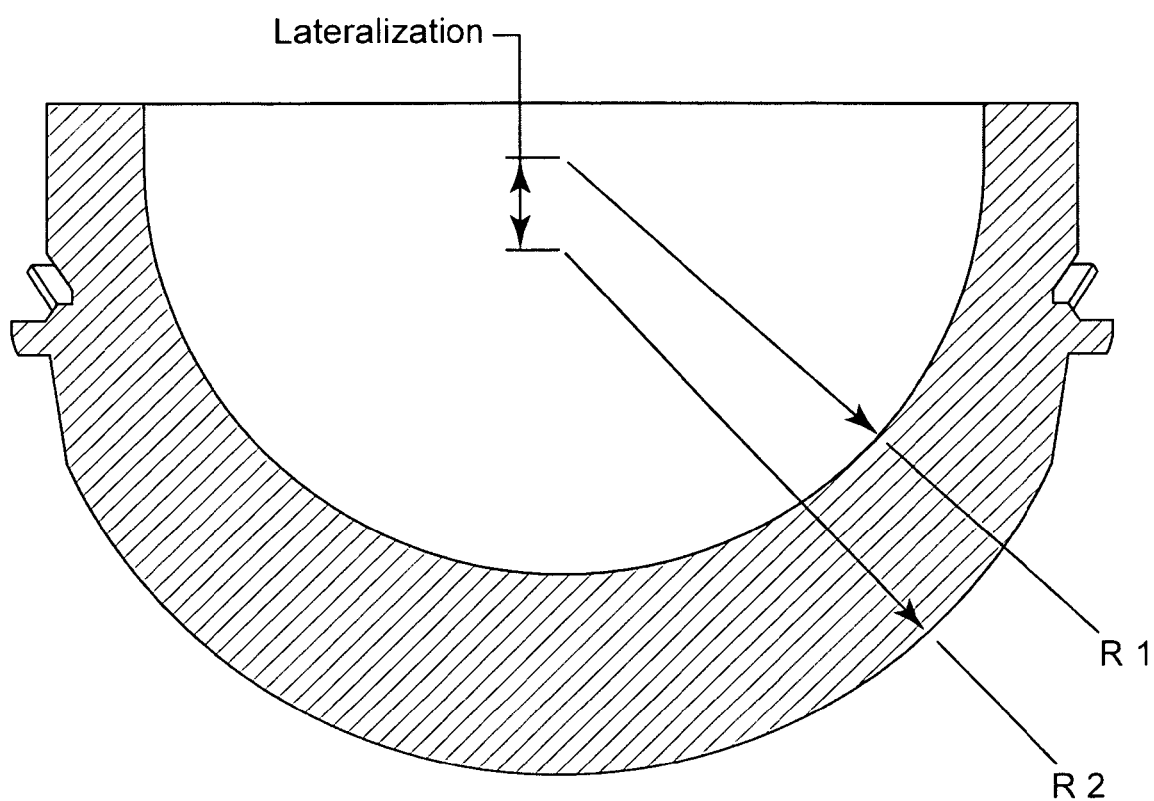

In some embodiments, the liner may have its center of rotation of the internal diameter a lateralized, or shifted (e.g., shifted laterally, by 4 mm). This means that there is a lateral shift between the inner radius and the outer radius of the liner. A liner without a lateral shift is shown in FIG. 23, and a liner with a lateral shift is shown in FIG. 24. As shown, it is possible for the outer radius to be lateralized downwardly to increase the thickness of the liner in order for the liner to accept a femoral head of a certain size (in the inner radius) but still have additional thickness (outer radius) to maintain strength. In other embodiments, the variable geometry rim surface may be used with a nonlateralized liner, with a liner lateralized by up to 8 mm, or with a liner that is lateralized differently. As used herein and as understood by those of skill in the art, "lateralized" refers to a liner wherein the center of the internal concave surface, or internal diameter, has been shifted laterally, or laterally and somewhat inferiorly, with respect to how the liner is oriented in a patient. In another embodiment, a variable geometry rim surface is used with a liner wherein the center of the internal concave surface, or internal diameter has been shifted medially by up to 4 mm.

Figure 25:
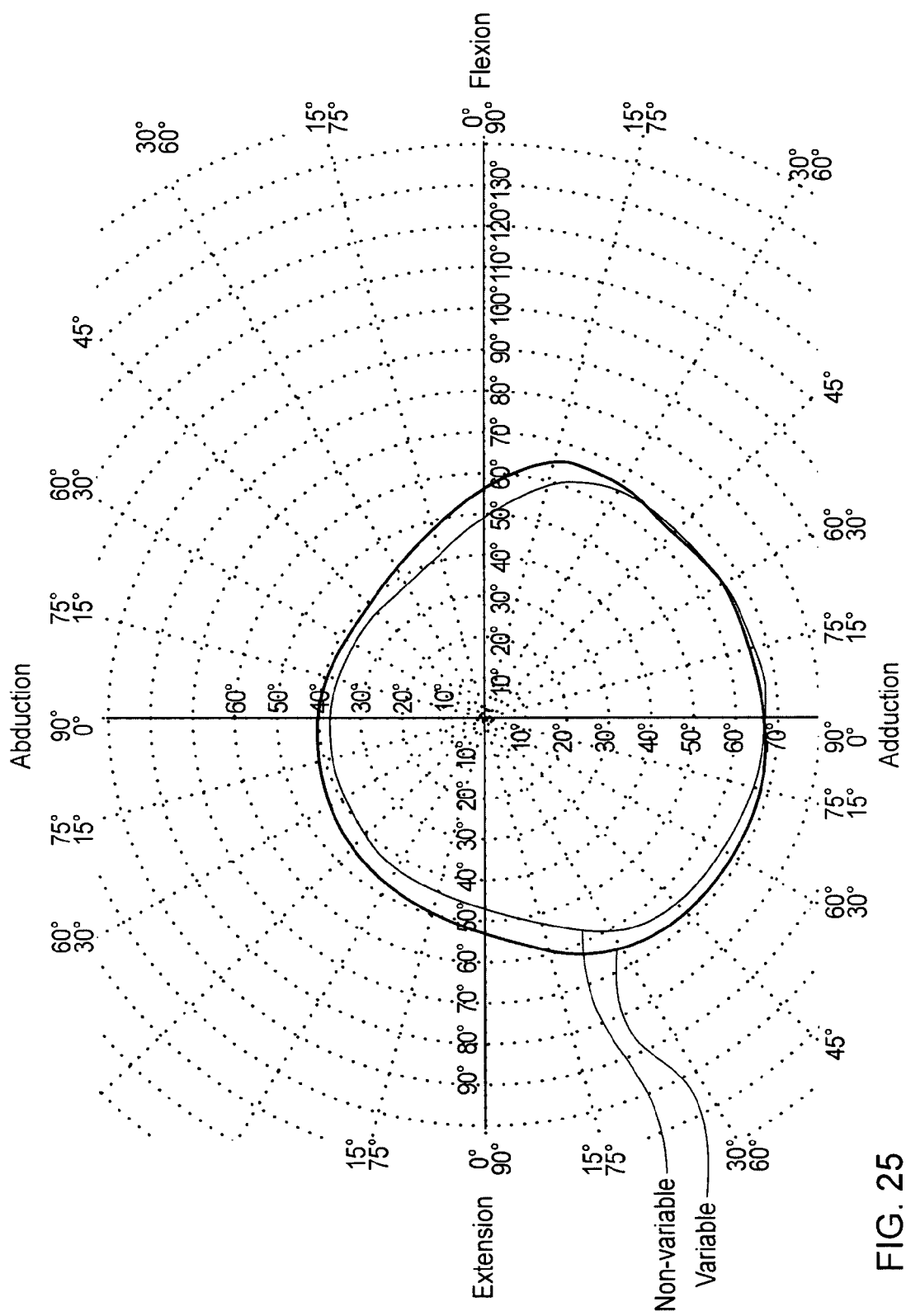
FIG. 25 is a graph showing a range of motion envelope for a variable geometry rim surface constrained liner according to various embodiments of this invention and a range of motion envelope of a non-variable geometry rim surface constrained liner.

Providing a constrained liner 20 with a rim 54 having an angle 27 that changes continuously also changes the amount that the femoral head is captured. As shown in FIG. 25, a variable angle constrained liner provides a greater range of motion than a traditional constrained liner provides. FIG. 25 graphically illustrates the comparison of range of motion of a variable angle chamfer constrained liner according to various embodiments of this invention, and range of motion of a prior art liner with a constant chamfer angle. Both liners in this example have a 32 mm internal diameter, and in both liners the center of the internal diameter is lateralized by 4 mm and the opening of the internal diameter is anteverted by 20°. The femoral component used with both liners was a size 14 Smith & Nephew Synergy® Stem, measuring 160 mm in length and with a 32 mm diameter head.

The solid line curve shown in FIG. 25 illustrates an example of a range of motion envelope that was derived using the below-described method for varying the rim surface geometry. This range of motion was characterized by components of flexion-extension and abduction-adduction. The dotted line is an example of a range of motion envelope provided by a non-variable, i.e. constant, geometry rim surface liner. On this graph the zero point, or anatomically neutral point, represents a liner oriented at 45° of abduction and 20° of anteversion and a femoral component oriented at 7° of adduction and 20° of anteversion. From this point the femoral component is rotated, as in a patient after implantation, about various anatomically relevant axes located, in this case, 15 degrees apart in a transverse plane of the body, to define the limit of range of motion about each axis. The purpose is to enlarge the surface that defines the outer limits or extent of the range of motion.

This can be demonstrated by placing FIG. 25 face-up on the floor with the flexion axis pointed forward, i.e. anteriorly, and standing above it with the left foot positioned on top of the graph and aligned with the flexion/extension axis. Rotating the left leg forward, in flexion, the limit of motion to liner rim impingement is approximately 60° with the variable angle chamfer liner, but only about 51° with the prior art constant angle chamfer liner. Rotating the leg backwards about the same axis, in extension, the limit of motion to liner rim contact is about 52° with the variable chamfer angle liner and about 48° with the prior art constant angle chamfer liner. This procedure was repeated, rotating a femoral component about axes located 15 degrees apart, thereby generating a range of motion envelope for both the variable angle chamfer liner and prior art constant angle chamfer liner shown by the solid and dotted line curves, respectively. As can be seen, the range of motion provided by the liner according to the present invention is superior.

Figure 26:
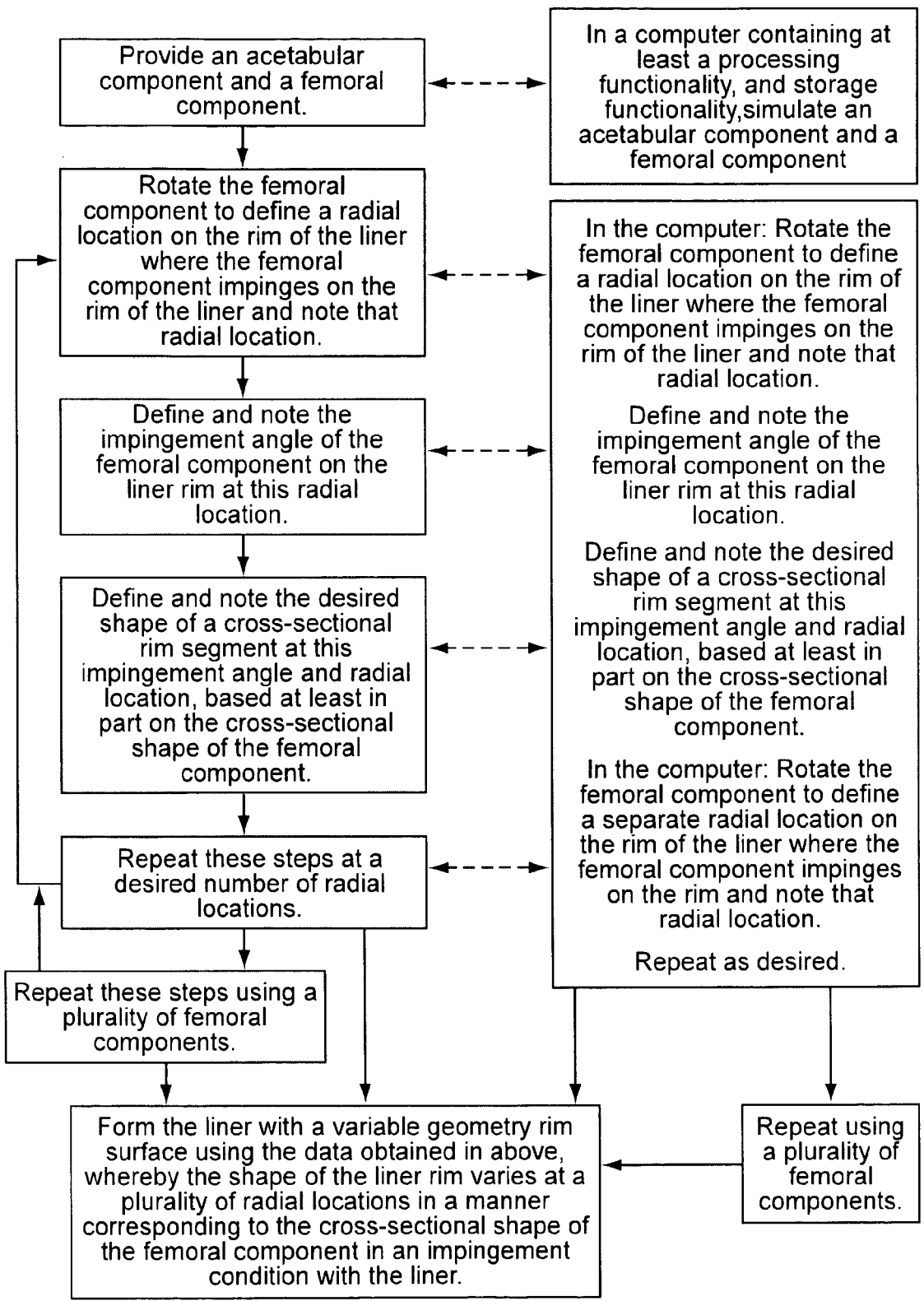
FIG. 26 is a flow chart outlining the steps for making variable geometry rim surface liner.

One method according to this invention seeks to determine orientation of a femoral component against the surface that defines the outer limits or extent of the range of motion to the liner rim geometry in order to optimize the maximum range of motion. As an example, one method according to the invention is shown in FIG. 26 and may be performed manually or with the aid of a computer, as described below.

1. Provide an acetabular component and a femoral component comprising a head, neck and stem. Preferably, provide an acetabular shell, a constrained liner, and a femoral component. Alternatively, introduce data corresponding to a three dimensional model of a constrained liner and femoral component into a computer containing a processing functionality, storage functionality, and rendering functionality. More preferably, introduce information corresponding to the acetabular shell, constrained liner, and femoral component.

2. From an anatomic neutral position, rotate the femoral component within the internal concave surface of the constrained liner to define a radial location on the rim of the liner where the femoral component contacts the outer limits or extent of the range of motion at the rim of the liner. If using a computer, the computer models and/or simulates the configuration of the shell, liner and femoral component and simulates the rotation of the femoral component until the femoral component reaches the outer limit of the range of motion at the rim of the liner at a defined radial location.

3. With the femoral component in this position, note the radial location and define the outer limit or extent of the range of motion of the femoral component in that position at that radial location on the rim.

4. Record the structure and orientation of this angle at this radial location. Define the location and desired shape of a cross-sectional rim segment at this outer limit and radial location, based at least in part on the cross-sectional shape of the femoral component where it reaches the outer limit of the range of motion at the rim at this radial location, and note this desired shape.

5. Rotate the femoral component within the constrained liner to define a separate radial location on the rim of the liner where the femoral component reaches the outer limit of the range of motion on the rim. In the computer example, the computer simulates the movement of the femoral component and may record the radial location.

6. Repeat steps three through five for a desired number of radial locations around the rim. In the computer simulation, the computer may track the data corresponding to the outer limit of the range of motion and cross-sectional shape of the femoral component at the outer limit with the liner at each of a plurality of radial locations around the rim.

Figure 27:
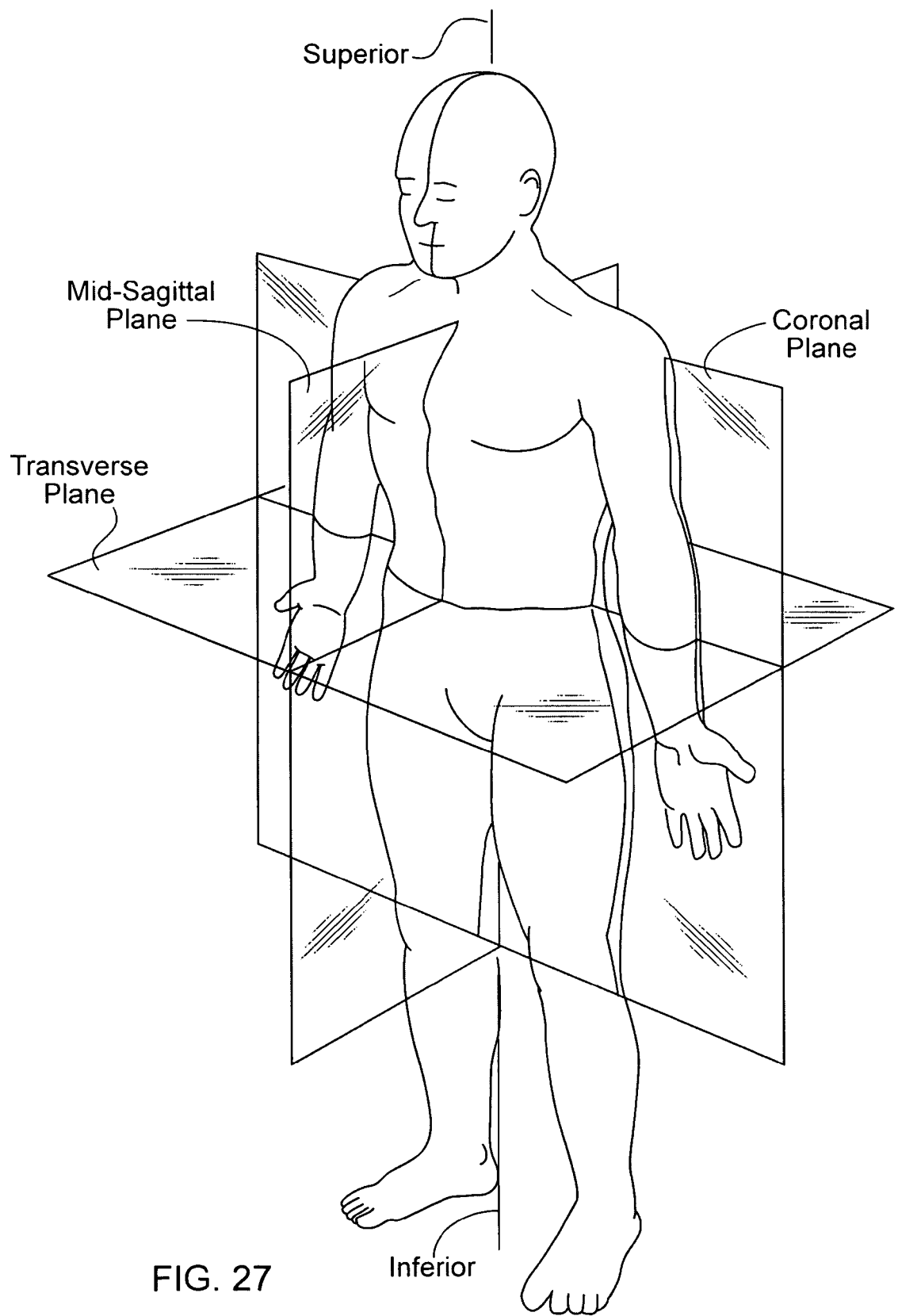
FIG. 27 is a diagram showing coronal, saggital and transverse planes of the body.

In one example rotate, or simulate the rotation of, the femoral component within the constrained liner relative to a relevant anatomical axis of the body. Preferably, rotate the femoral component relative to anatomically relevant axes running through the center of rotation of a femoral component articulating within the internal concave surface of the liner, and oriented in a plane substantially parallel to transverse, coronal or saggital planes of the body. These planes are shown in FIG. 27. More preferably, rotate or simulate the rotation of the femoral component about axes that are fifteen degrees apart in said planes.

7. Repeat, if desired, steps 1-6, with different femoral component head offsets possible in the assembly of the stem and head to obtain a range of angles that define the outer limit or extent of the range of motion and a cross-sectional envelope determined by the group of angles defining the outer limits and cross-sectional shapes corresponding to the plurality of femoral components used. Preferably, repeat steps 1-6 with any other structural variations in a set of stem, shell, and liner products or liners.

8. Form the constrained liner with the variable geometry rim surface using the data obtained in steps 1-6, or through step 7 if desired, and form the liner such that the shape of the liner rim varies at a plurality of radial locations in a manner corresponding to the cross-sectional shape of the femoral components where it reaches the outer limit of the range of motion with the liner.

The geometry of the rim surface may be defined in part by using some or all of these data relating to the specified angles defining the outer limit of the range of motion and cross-sectional envelopes determined in steps 3-6. It may also, and in some cases additionally, be defined by specifying the rim surface geometry of the liner to be formed by doing necessary or desired extrapolation, interpolation, or estimation based on the angles defining the outer limit of the range of motion and locational data from steps 3-6. In the computer simulation example, the computer may define the geometry of the rim based at least in part on the angles defining the outer limit of the range of motion, cross-sectional envelope, and locational data obtained in the steps outlined above or on extrapolation, interpolation or estimation therefrom. The computer may produce a set of specifications based on the data obtained in the steps above for forming a liner with a variable geometry rim surface.

All of these steps are subject to the design goals of creating a rim surface optimized for range of motion of the femoral component relative to the liner. More preferably, all of these steps are subject to taking into account other anatomical, performance, durability and structural criteria.

FIG. 26 shows a functional block diagram illustrating the process described above for making the variable geometry rim surface liner of the present invention. The manual method is outlined on the left side of the flow chart, while the right side outlines the computer simulation example. If computer simulated, the computer may have a hardware environment, or system, in which the simulation method of the present invention may be performed. It may comprise a processor capacity, a mass memory capacity, and an input/output capacity. Any or all functionalities described may be implemented or reside on one or more "computers," processors, platforms, networks or other systems.

Steps 1-6 outlined above were performed on Unigraphics® brand computer aided design package which used the data to produce an image of a three-dimensional solid model liner with a variable chamfer rim geometry. Any device design software or software which can be used to design objects, running on any desired platform using any operating system, whether or not network based, can be used in accordance with the present invention. Also produced was a code corresponding to the specification of this liner which was used to program a machine tool, such as a 5-axis CNC milling machine, to form the liner.

As follows from the method of determining optimized chamfer angles described above, at the points where the neck 28 is more likely to contact the outer edge of the chamfer 26, the angle 27 is made more obtuse in order to produce a condition where the femoral neck contacts the inner and outer edges of the chamfer at the same time, thus allowing a broader range of motion. Where the neck 28 is likely to contact only the inner edge, the angle 27 is made more acute to produce a condition where the femoral neck contacts the inner and outer edges of the chamfer at the same time. The condition of contact in which the neck will require the widest chamfer angle is isolated, resulting in a chamfer angle that is customized for the neck geometry of the femoral component.

In another embodiment, the variable angle 27 of liner 20 is made to correspond to any shaped stem neck so that the varying angle 27 is optimized for a neck with a particular geometry, such as cylindrical. Different liner rim surface geometries may be used depending upon the particular neck geometry.

Constrained liners of various embodiments of the present invention may be formed of various materials, including but not limited to ceramic, metal, polyethylene, ultra high molecular weight polyethylene, and highly cross-linked ultra high molecular weight polyethylene, more preferably ultra high molecular weight polyethylene. They are typically used in combination with a metallic shell (e.g., titanium, stainless steel, cobalt chromium, alloys thereof, or any other appropriate biocompatible material). However, the liners may also be implanted directly into the acetabulum of a patient. When implanted directly into the acetabulum, the liners are generally secured into the acetabulum with bone cement. The liners also may be mechanically fixed within the acetabulum by bone screws or screw threads on the external surface of the liner. Another method of securing the liner in the acetabulum is by providing a bone in-growth surface which is integral to the external surface of the liner. This surface may be molded into or otherwise integral to the external surface of the liner. This integral bone in-growth surface may be made by creating a roughened area on the external surface of the liner. This integral bone in-growth surface may also comprise a textured matrix which is incorporated into the material of the external surface of the liner; such a matrix may include metal porous beads, fiber mesh, or other surfaces which provide a scaffold into which the patient's bone will grow, thereby physically securing the liner within the acetabulum.

The liners described above may also be provided as a family of variable angle constrained liners, a family of variable angle anteverted liners, and so forth, in order to provide the surgeon with the widest range of options during surgery. They may be provided as a series of separate kits (e.g., a kit containing different sizes of variable angle constrained liners only), or as different types of liners provided together (e.g., a kit containing different sizes of variable angle constrained liners, different sizes of variable angle anteverted liners, and so forth).

The foregoing description of the embodiments of the invention has been presented only for the purpose of illustration and description and is not intended to be exhaustive or to limit the invention to the precise forms disclosed. Many modifications and variations are possible in light of the above teaching. The embodiments were chosen and described in order to explain the principles of the invention and their practical application so as to enable others skilled in the art to utilize the invention and various embodiments and with various modifications as are suited to the particular use contemplated.

What is claimed is:

1. A constrained liner having a central axis, comprising:
    (a) an internal concave surface of the constrained liner having an opening adapted to receive a head of a femoral component, wherein the internal concave surface provides greater than hemispherical coverage of the head at a constraining portion of the constrained liner;
    (b) an external surface positioned on an opposing side of the internal concave surface; and
    (c) a rim located at the opening of the internal concave surface, the rim comprising a variable angle chamfer surface separate from the constraining portion, the variable angle chamfer surface forming at least a portion of the rim that varies angularly with respect to the central axis of the constrained liner around the rim.

2. The constrained liner of claim 1, wherein the variable angle chamfer surface is defined at least in part by, given a desired angular position of the liner in a patient,
    one or more angles, each angle defined by a point on the rim at an outer limit of the range of motion, of at least one femoral component whose head is adapted to be received in the internal concave surface of the liner measured relative to the central axis of the constrained liner;
    wherein the one or more angles of the variable angle chamfer surface vary around the rim of the liner in a manner corresponding to the cross-sectional shape of the portion of the at least one femoral component that is in an impingement condition with the liner.

3. The constrained liner of claim 1, wherein the liner is anteverted, neutral, or offset.

4. The constrained liner of claim 1, wherein the variable angle chamfer surface comprises a plurality of variable angles.

5. The constrained liner of claim 1, wherein the variable angle chamfer surface comprises a face having a series of various angles that change substantially continuously along the rim surface.

6. The constrained liner of claim 1, wherein the variable angle chamfer surface comprises a plurality of variable angles, each of the plurality of variable angles defined as an angle at any point on or near the rim of the liner at which the surface of the chamfer is positioned relative to the central axis of the opening of the internal diameter of the liner.

7. The constrained liner of claim 1, wherein the variable angle chamfer surface is defined at least in part by, at each of a plurality of locations around the rim, an angle determined using a group of impingement angles corresponding to a plurality of femoral components in an impingement condition with the constrained liner whose heads are adapted to be received in the internal concave surface of the liner.

8. The constrained liner of claim 1, wherein the variable angle chamfer surface varies around the rim of the liner and is symmetric about a plane.

9. The constrained liner of claim 1, wherein the constrained liner is a one-piece liner.

10. The constrained liner of claim 1, wherein the central axis is offset from a center of a surface in which the liner is adapted to be received.

11. The constrained liner of claim 1, wherein the center of the internal concave surface is shifted laterally by up to 10mm.

12. The constrained liner of claim 1, wherein the central axis is anteverted with respect to a surface in which the liner is adapted to be received.

13. The constrained liner of claim 1, wherein the variable angle chamfer surface defines an impingement angle at each of a plurality of radial locations around the rim of the liner that is specified by a computer simulation of a constrained liner and a femoral component, wherein the computer simulates rotation of the femoral component within the liner to define a radial location on the rim of the liner where the femoral component impinges on the rim, and determines the impingement angle and cross-sectional shape of the femoral component on the rim at that radial location.

14. The constrained liner of claim 1, wherein the variable angle chamfer surface defines an impingement angle at each of a plurality of radial locations around the rim of the liner that is specified by manually rotating the femoral component within a constrained liner to define a radial location on the rim of the liner where the femoral component impinges on the rim, and determining the impingement angle and cross-sectional shape of the femoral component on the rim at that radial location.

15. The constrained liner of claim 1, wherein the shape of the variable angle chamfer surface varies around the rim of the liner in a manner corresponding to a cross-sectional shape formed by a femoral component that is in an impingement condition with the rim of the constrained liner.

16. The constrained liner of claim 1, wherein the variable angle chamfer surface comprises a plurality of variable angle segments.

17. The constrained liner of claim 1, wherein the variable angle chamfer surface comprises a plurality of constant angle segments.

18. The constrained liner of claim 1, wherein the constrained liner provides more than hemispherical coverage and the variable angle chamfer surface allows the constrained liner to receive a head of a femoral component while also providing a greater range of motion than that provided by a constrained liner without a variable angle chamfer surface.

19. The constrained liner of claim 1, wherein the central axis is anteverted at about 15 degrees with respect to a surface in which the liner is adapted to be received.

20. The constrained liner of claim 1, wherein the variable angle chamfer surface comprises a plurality of variable angles, and wherein each of the plurality of variable angles range from about 100 degrees to about 200 degrees.

21. The constrained liner of claim 1, wherein the variable angle chamfer surface varies around the rim of the liner and is asymmetric about a plane.

22. The constrained liner of claim 1, wherein the liner further comprises a hood member.

23. A prosthetic device comprising:
(a) an acetabular shell comprising an internal concave surface adapted to receive a constrained liner and an external surface adapted to be received in an acetabulum; and
(b) a constrained liner having:
  (i) an internal concave surface of the constrained liner having an opening adapted to receive a head of a femoral component, wherein the internal concave surface provides greater than hemispherical coverage of the head at a constraining portion of the constrained liner;
  (ii) an external surface positioned on an opposing side of the internal concave surface; and
  (iii) a rim located at the opening of the internal concave surface, the rim comprising a variable angle chamfer surface separate from the constraining portion, the variable angle chamfer surface forming at least a portion of the rim that varies angularly with respect to the central axis of the constrained liner around the rim.

24. The prosthetic device of claim 23, wherein the wherein the constrained liner provides more than hemispherical coverage and the variable angle chamfer surface allows the constrained liner to receive a head of a femoral component, while also providing a greater range of motion than that provided by a constrained liner without a variable angle chamfer surface.

25. A method of replacing a hip joint in a patient comprising:
(a) providing a constrained liner having:
  (i) an internal concave surface of the constrained liner having an opening adapted to receive a head of a femoral component, wherein the internal concave surface provides greater than hemispherical coverage of the head at a constraining portion of the constrained liner;
  (ii) an external surface positioned on an opposing side of the internal concave surface; and
  (iii) a rim located at the opening of the internal concave surface, the rim comprising a variable angle chamfer surface separate from the constraining portion, the variable angle chamfer surface forming at least a portion of the rim that varies angularly with respect to the central axis of the constrained liner around the rim,
(b) providing an acetabular shell comprising an internal concave surface adapted to receive the liner and an external surface adapted to be received in an acetabulum;
(c) surgically implanting and securing the shell in the acetabulum of a patient;
(d) securing the liner in the internal concave surface of the shell;
(e) providing a femoral component, comprising a head, neck and a stem, wherein the head is adapted to articulate within the internal concave surface of the liner;
(f) surgically implanting the stem of the femoral component into the femur of a patient; and
(g) installing the head of the femoral component into the internal concave surface of the liner.

26. The method of claim 23, wherein the constrained liner provides more than hemispherical coverage and the variable angle chamfer surface allows the constrained liner to receive a head of a femoral component, while also providing a greater range of motion than that provided by a constrained liner without a variable angle chamfer surface.

* * * * *